United States Patent
Fukuzaki et al.

(10) Patent No.: US 10,529,927 B2
(45) Date of Patent: Jan. 7, 2020

(54) ORGANIC THIN FILM TRANSISTOR, METHOD OF MANUFACTURING ORGANIC THIN FILM TRANSISTOR, ORGANIC THIN FILM TRANSISTOR MATERIAL, ORGANIC THIN FILM TRANSISTOR COMPOSITION, ORGANIC SEMICONDUCTOR FILM, AND COMPOUND

(71) Applicants: FUJIFILM Corporation, Tokyo (JP); THE UNIVERSITY OF TOKYO, Tokyo (JP)

(72) Inventors: Eiji Fukuzaki, Kanagawa (JP); Hiroaki Tsuyama, Kanagawa (JP); Masashi Koyanagi, Kanagawa (JP); Yoshihisa Usami, Kanagawa (JP); Tetsuya Watanabe, Kanagawa (JP); Toshihiro Okamoto, Tokyo (JP); Junichi Takeya, Tokyo (JP)

(73) Assignees: FUJIFILM Corporation, Tokyo (JP); THE UNIVERSITY OF TOKYO, Tokyo (JP)

( * ) Notice: Subject to any disclaimer, the term of this patent is extended or adjusted under 35 U.S.C. 154(b) by 88 days.

(21) Appl. No.: 15/884,537

(22) Filed: Jan. 31, 2018

(65) Prior Publication Data
US 2018/0159043 A1    Jun. 7, 2018

Related U.S. Application Data

(63) Continuation of application No. PCT/JP2016/072584, filed on Aug. 2, 2016.

(30) Foreign Application Priority Data

Aug. 4, 2015  (JP) .................................. 2015-154355

(51) Int. Cl.
*H01B 1/00* (2006.01)
*H01L 51/00* (2006.01)
(Continued)

(52) U.S. Cl.
CPC ........ *H01L 51/0053* (2013.01); *C07D 495/16* (2013.01); *C07D 517/16* (2013.01);
(Continued)

(58) Field of Classification Search
CPC . H01B 1/00; H01B 1/12; H01B 1/121; H01B 1/124; H01L 51/05; H01L 51/30;
(Continued)

(56) References Cited

U.S. PATENT DOCUMENTS

2008/0300405 A1    12/2008 Konemann
2011/0155247 A1    6/2011 Quinn et al.
(Continued)

FOREIGN PATENT DOCUMENTS

EP    2492271 A1    8/2012
JP    2013-515785 A    5/2013
(Continued)

OTHER PUBLICATIONS

Subashani Maniam et al., "Unusual Products from Oxidation of Naphthalene Diimides", Asian Journal of Organic Chemistry, Feb. 2, 2016, pp. 490-493, vol. 5, No. 4, Germany.
(Continued)

*Primary Examiner* — Mark Kopec
(74) *Attorney, Agent, or Firm* — Studebaker & Brackett PC

(57) ABSTRACT

An object of the present invention is to provide an organic thin film transistor having excellent carrier mobility and excellent atmospheric stability, a novel compound, an organic thin film transistor material, an organic semicon-
(Continued)

ductor film, an organic thin film transistor composition, and a method of manufacturing an organic thin film transistor using this. The organic thin film transistor according to the present invention has an organic semiconductor film containing a compound represented by Formula (1) or (2).

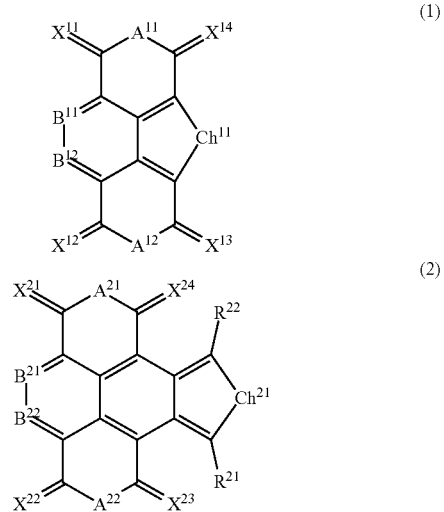

22 Claims, 2 Drawing Sheets

(51) Int. Cl.
*C07D 495/12* (2006.01)
*C07D 517/12* (2006.01)
*C07D 495/16* (2006.01)
*C07D 517/16* (2006.01)
*H01L 29/786* (2006.01)
*C09B 57/08* (2006.01)
*H01B 1/12* (2006.01)
*H01L 51/05* (2006.01)

(52) U.S. Cl.
CPC ............... *C09B 57/08* (2013.01); *H01B 1/12* (2013.01); *H01L 29/786* (2013.01); *H01L 51/0071* (2013.01); *H01L 51/0074* (2013.01); H01L 51/0545 (2013.01); H01L 51/0558 (2013.01)

(58) Field of Classification Search
CPC ...... H01L 51/40; C07D 409/14; C07D 421/14; C07D 495/12; C07D 495/22; C07D 517/12; C07D 517/16
See application file for complete search history.

(56) References Cited

U.S. PATENT DOCUMENTS

| 2014/0231773 | A1 | 8/2014 | Suraru et al. |
| 2016/0104842 | A1 | 4/2016 | Takeya et al. |
| 2018/0159053 | A1* | 6/2018 | Koyanagi ............. C07F 7/1804 |
| 2018/0205021 | A1* | 7/2018 | Koyanagi ............... C09B 57/00 |

FOREIGN PATENT DOCUMENTS

| JP | 2013-207085 A | 10/2013 |
| JP | 2013-234185 A | 11/2013 |
| JP | 2014-532035 A | 12/2014 |
| WO | 2010/111822 A1 | 10/2010 |
| WO | 2011/082234 A1 | 7/2011 |
| WO | 2014/174435 A2 | 10/2014 |
| WO | 2014/175351 A1 | 10/2014 |
| WO | 2014/178415 A1 | 11/2014 |

OTHER PUBLICATIONS

Extended European Search Report issued by the European Patent Office dated Aug. 2, 2018, which corresponds to EP16833014.0-1110 and is related to U.S. Appl. No. 15/884,537.
International Search Report issued in PCT/JP2016/072584; dated Sep. 13, 2016.
Written Opinion issued in PCT/JP2016/072584; dated Sep. 13, 2016.

* cited by examiner

ORGANIC THIN FILM TRANSISTOR, METHOD OF MANUFACTURING ORGANIC THIN FILM TRANSISTOR, ORGANIC THIN FILM TRANSISTOR MATERIAL, ORGANIC THIN FILM TRANSISTOR COMPOSITION, ORGANIC SEMICONDUCTOR FILM, AND COMPOUND

CROSS-REFERENCE TO RELATED APPLICATIONS

This application is a Continuation of PCT International Application No. PCT/JP2016/072584 filed on Aug. 2, 2016, which claims priority under 35 U.S.C. § 119(a) to Japanese Patent Application No. 2015-154355 filed on Aug. 4, 2015. The above application is hereby expressly incorporated by reference, in its entirety, into the present application.

BACKGROUND OF THE INVENTION

1. Field of the Invention

The present invention relates to an organic thin film transistor, a method of manufacturing an organic thin film transistor, an organic thin film transistor material, an organic thin film transistor composition, an organic semiconductor film, and a compound.

2. Description of the Related Art

Since light weight, low cost, and flexibility can be obtained, an organic thin film transistor (organic TFT (thin film transistor)) having an organic semiconductor film (organic semiconductor layer) is used in a device using a logic circuit such as a field effect transistor (FET), a radio frequency identifier (RFID: RF tag), or a memory used in a liquid crystal display or an organic electro luminescence (EL) display.

As a compound for forming such an organic semiconductor film, JP2013-515785A discloses an organic semiconductive compound mainly having N-functionalized fused ring (aromatic) imide which is oxidized by thione.

SUMMARY OF THE INVENTION

Recently, in view of improving the performance of the organic thin film transistor, further improvement of the mobility of the organic thin film transistor and excellent atmospheric stability are required. Here, the atmospheric stability refers to carrier mobility in a case where an organic thin film transistor has been left for a predetermined period in the atmosphere at room temperature (about 23° C.).

In these circumstances, the present inventors have conducted research on a compound (organic semiconductor material) having a naphthalene diimide skeleton among compounds disclosed in JP2013-515785A, depending on the types thereof, the carrier mobility and the atmospheric stability in a case where this compound was used in an organic semiconductor film of an organic semiconductor thin film transistor were not sufficient in some cases, and thus did not satisfy the level necessarily required in these days.

Here, an object of the present invention is to provide an organic thin film transistor having excellent carrier mobility and excellent atmospheric stability.

Another object of the present invention is to provide a novel compound and an organic thin film transistor material, an organic thin film transistor composition, and an organic semiconductor film which contain this compound.

Another object of the present invention is to provide a method of manufacturing an organic thin film transistor using the organic thin film transistor composition.

As a result of intensive studies on the above problems, the present inventors have found that a desired effect can be obtained by using a compound represented by Formula (1) or (2) described below, so as to conceive the present invention.

That is, the present inventors have found that the aforementioned objects can be achieved with the following configurations.

[1] An organic thin film transistor comprising an organic semiconductor film containing a compound represented by Formula (1) or (2).

[2] The organic thin film transistor according to [1], in which, in Formula (1), $Ch^{11}$ is a sulfur atom or a selenium atom, and in which, in Formula (2), $Ch^{21}$ is a sulfur atom or a selenium atom.

[3] The organic thin film transistor according to [1] or [2], in which, in Formula (1), all of $X^{11}$, $X^{12}$, $X^{13}$, and $X^{14}$ are oxygen atoms, and in which, in Formula (2), all of $X^{21}$, $X^{22}$, $X^{23}$, and $X^{24}$ are oxygen atoms.

[4] The organic thin film transistor according to any one of [1] to [3], in which, in Formula (1), $A^{11}$ and $A^{12}$ each independently represent —N($R^N$)—, and in which, in Formula (2), $A^{21}$ and $A^{22}$ each independently represent —N($R^N$)—.

[5] The organic thin film transistor according to [4], in which $R^N$ is a linear, branched, or cyclic alkyl group having 1 to 20 carbon atoms, an aryl group having 6 to 20 carbon atoms, or a heteroaryl group having 3 to 20 carbon atoms.

[6] The organic thin film transistor according to [5], in which $R^N$ is a cyclic alkyl group having 4 to 6 carbon atoms.

[7] The organic thin film transistor according to any one of [1] to [6], in which, in a case where at least one of $B^{11}$ or $B^{12}$ in Formula (1) is —C($R^M$)=, at least one of $R^M$'s is a halogen atom, and in which, in a case where at least one of $B^{21}$ or $B^{22}$ in Formula (2) is —C($R^M$)=, at least one of $R^M$'s is a halogen atom.

[8] The organic thin film transistor according to any one of [1] to [7], in which, $R^{21}$ and $R^{22}$ in Formula (2) each independently represent a hydrogen atom, a methyl group, a halogen atom, or a cyano group.

[9] A compound represented by Formula (1) or (2).

[10] The compound according to [9], in which, in Formula (1), $Ch^{11}$ is a sulfur atom or a selenium atom, and in which, in Formula (2), $Ch^{21}$ is a sulfur atom or a selenium atom.

[11] The compound according to [9] or [10], in which, in Formula (1), all of $X^{11}$, $X^{12}$, $X^{13}$, and $X^{14}$ are oxygen atoms, and in which, in Formula (2), all of $X^{21}$, $X^{22}$, $X^{23}$, and $X^{24}$ are oxygen atoms.

[12] The compound according to any one of [9] to [11], in which, in Formula (1), $A^{11}$ and $A^{12}$ each independently represent —N($R^N$)— or —P($R^N$)—, and in which, in Formula (2), $A^{21}$ and $A^{22}$ each independently represent —N($R^N$)— or —P($R^N$)—.

[13] The compound according to any one of [9] to [12], in which, in Formula (1), $A^{11}$ and $A^{12}$ each independently represent —N($R^N$)—, and in which, in Formula (2), $A^{21}$ and $A^{22}$ each independently represent —N($R^N$)—.

[14] The compound according to [12] or [13], in which $R^N$ is a linear, branched, or cyclic alkyl group having 1 to 20 carbon atoms, an aryl group having 6 to 20 carbon atoms, or a heteroaryl group having 3 to 20 carbon atoms.

[15] The compound according to [14], in which $R^N$ is a cyclic alkyl group having 4 to 6 carbon atoms.

[16] The compound according to any one of [9] to [15], in which, in a case where at least one of $B^{11}$ or $B^{12}$ in Formula (1) is —C($R^M$)═, at least one of $R^M$'s is a halogen atom, and in which, in a case where at least one of $B^{21}$ or $B^{22}$ in Formula (2) is —C($R^M$)═, at least one of $R^M$'s is a halogen atom.

[17] The compound according to any one of [9] to [16], in which, $R^{21}$ and $R^{22}$ in Formula (2) each independently represent a hydrogen atom, a methyl group, a halogen atom, or a cyano group.

[18] An organic thin film transistor material comprising the compound according to any one of [9] to [17].

[19] An organic thin film transistor composition comprising the compound according to any one of [9] to [17].

[20] The organic thin film transistor composition according to [19], further comprising: a binder polymer.

[21] An organic semiconductor film containing: the compound according to any one of [9] to [17].

[22] A method of manufacturing an organic thin film transistor, comprising: a step of coating a substrate with the organic thin film transistor composition according to [19] or [20] and drying the composition to form an organic semiconductor film.

As described above, according to the present invention, it is possible to provide an organic thin film transistor having excellent carrier mobility and excellent atmospheric stability.

According to the present invention, it is possible to provide a novel compound and an organic thin film transistor material, an organic thin film transistor composition, and an organic semiconductor film which contain this compound.

According to the present invention, it is possible to provide a method of manufacturing an organic thin film transistor using the organic thin film transistor composition.

DESCRIPTION OF THE PREFERRED EMBODIMENTS

Figure 1:
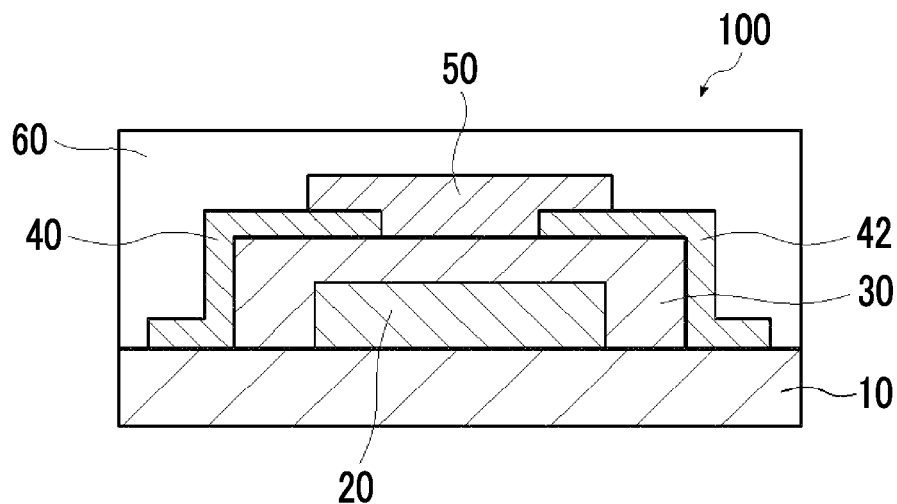
FIG. 1 is a cross-sectional view schematically illustrating a bottom contact type organic thin film transistor according to one embodiment of the present invention.

Hereinafter, the present invention will be described in detail.

In the present specification, the numerical range expressed by using "to" means a range including numerical values described before and after "to" as a lower limit value and an upper limit value.

In the present specification, in a case where there is no description regarding whether a group (atomic group) is substituted or unsubstituted, the group includes both of a group having a substituent and a group not having a substituent. For example, an "alkyl group" includes not only an alkyl group not having a substituent (unsubstituted alkyl group) but also an alkyl group having a substituent (substituted alkyl group).

In the present specification, a combination of preferable aspects is a more preferable aspect.

[Organic Thin Film Transistor]

An organic thin film transistor according to the present invention has an organic semiconductor film containing a compound represented by Formula (1) or (2).

As a result of intensive research, the present inventors have found that an organic thin film transistor having excellent carrier mobility and excellent atmospheric stability can be obtained by using a compound represented by Formula (1) or (2). Details of the reason are not clarified, the following reasons are assumed.

That is, the compounds represented by Formulae (1) and (2) have a quinoid structure, and thus Lowest Unoccupied Molecular Orbital (LUMO) tends to be lower than that of ordinary naphthalenes. That is, the compounds represented by Formulae (1) and (2) have a structure in which a portion of the naphthalene diimide skeleton is substituted with isobenzothiophene (2-benzothiophene) or the like, and thus has lower LUMO than the structure before substitution.

As a result, it is presumed that the synergistic action of the functions resulting from such a structure will further lower the LUMO such that an organic thin film transistor having excellent carrier mobility and excellent atmospheric stability can be obtained.

<Compound Represented by Formula (1)>

The compound represented by Formula (1) is a novel compound, and can be suitably used in an organic semiconductor film of an organic thin film transistor, and also can be used in other applications described below.

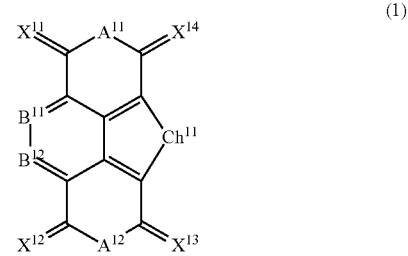

(1)

In Formula (1), $A^{11}$ and $A^{12}$ each independently represent —N($R^N$)—, —P($R^N$)—, or —O—. Among these, in view of improvement of the carrier mobility, $A^{11}$ and $A^{12}$ each independently and preferably represent —N($R^N$)— or —P($R^N$)— and more preferably represent —N($R^N$)—.

$R^N$ represents a hydrogen atom or a substituent. A plurality of $R^N$'s are identical to or different from each other.

In view of improvement of the carrier mobility, $A^{11}$ and $A^{12}$ are preferably the same group.

In the present specification, examples of the substituent include a halogen atom, an alkyl group, an alkenyl group, an alkynyl group, an aryl group, a heterocyclic group (which may be referred to as a heteroaryl group), a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, carbamoyl group, an arylazo group, a heterocyclic azo group, an imide group, a phosphino group, a phosphinyl group, a phosphinyloxy group, a phosphinylamino group, a phosphono group, a silyl group, a hydrazino group, a ureido group, a boronic acid group ($-B(OH)_2$), a phosphato group ($-OPO(OH)_2$), a sulfato group ($-OSO_3H$), a group derived from a structure represented by Formula (1), a group derived from a structure represented by Formula (2), and other well-known substituents. The substituent may be further substituted with a substituent.

Here, in the present specification, unless described otherwise, an "alkyl group" has any one of a straight chain shape, a branched shape, and a cyclic shape. Examples of the cyclic alkyl group include a cycloalkyl group, a bicycloalkyl group, and a tricycloalkyl group.

Among these, $R^N$ is preferably a hydrogen atom, a silyl group, a heterocyclic group, an aryl group, an alkynyl group, or a linear, branched, or cyclic alkyl group. Each group except for a hydrogen atom may be further substituted with a substituent.

Among these, in view of the improvement of the carrier mobility, $R^N$ is preferably a linear, branched, or cyclic alkyl group having 1 to 20 carbon atoms, an aryl group having 6 to 20 carbon atoms, or a heteroaryl group having 3 to 20 carbon atoms and more preferably a linear, branched, or cyclic alkyl group having 1 to 20 carbon atoms. Each group may be further substituted with a substituent.

In view of improvement of carrier mobility, $R^N$ is even more preferably a cyclic alkyl group (cycloalkyl group) having 3 to 8 carbon atoms (preferably 4 to 7 carbon atoms and more preferably 5 to 6 carbon atoms) and particularly preferably a cyclohexyl group.

In Formula (1), $B^{11}$ and $B^{12}$ each independently represent $-N=$ or $-C(RM)=$.

In view of improvement of the atmospheric stability, it is preferable that both of $B^{11}$ and $B^{12}$ are $-C(R^M)=$, or one is $-N=$ and the other is $-C(R^M)=$, it is more preferable that the both are $-C(R^M)=$.

In a case where both of $B^{11}$ and $B^{12}$ are $-C(R^M)=$, $R^M$ included in $B^{11}$ and $R^M$ included in $B^{12}$ may form a ring. In a case where a ring is formed, the ring is preferably an aromatic heterocyclic ring or an aromatic hydrocarbon ring, and more preferably a benzene ring. In a case where $R^M$ included in $B^{11}$ and $R^M$ included in $B^{12}$ form a ring, this ring may have the aforementioned substituent, and the substituents may be bonded to each other to further form a ring.

$R^M$ represents a hydrogen atom or a substituent. In Formula (1), in a case where a plurality of $R^M$'s exist, the plurality of $R^M$'s may be identical to or different from each other. Specific examples of the substituent in $R^M$ are the same as those of $R^N$ described above.

Among these, $R^M$ is preferably a hydrogen atom, a halogen atom, a halogenated alkyl group, a cyano group, a nitro group, an alkoxy group, an alkoxycarbonyl group, a carboxy group, a heterocyclic group, and an amino group, more preferably a hydrogen atom, a halogen atom, or a cyano group, and even more preferably a hydrogen atom or a cyano group.

Particularly, in Formula (1), at least one of $B^{11}$ or $B^{12}$ is $-C(R^M)=$, at least one of $R^M$'s is preferably a halogen atom or a cyano group and more preferably a cyano group, since atmospheric stability is improved.

In Formula (1), $Ch^{11}$ represents a sulfur atom, a sulfinyl group ($-SO-$), a sulfonyl group ($-SO_2-$), a selenium atom, a seleninyl group ($-SeO-$) or a selenonyl group ($-SeO_2-$). In view of improvement of carrier mobility, a sulfur atom or a selenium atom is preferable.

In Formula (1), $X^{11}$, $X^{12}$, $X^{13}$, and $X^{14}$ each independently represent an oxygen atom or a sulfur atom. In view of improvement of atmospheric stability, all of $X^{11}$, $X^{12}$, $X^{13}$, and $X^{14}$ are preferably oxygen atoms.

In view of improvement of carrier mobility and improvement of atmospheric stability, the compound represented by Formula (1) is preferably a compound represented by Formula (3), (4), or (5) and more preferably a compound represented by Formula (5).

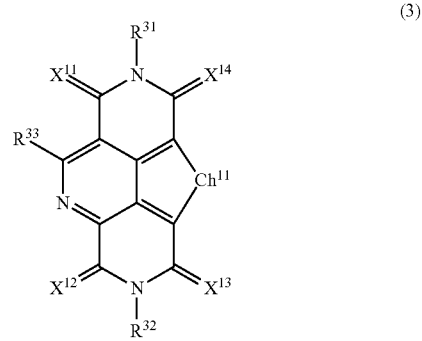

(3)

In Formula (3), $R^{31}$ and $R^{32}$ each independently represent a hydrogen atom, a linear, branched, or cyclic alkyl group having 1 to 20 carbon atoms, an aryl group having 6 to 20 carbon atoms, or a heteroaryl group having 3 to 20 carbon atoms. The preferable aspects of $R^{31}$ and $R^{32}$ are the same as that of $R^N$ in Formula (1).

In Formula (3), $R^{33}$ is a hydrogen atom, a halogen atom, or a cyano group. In view of improvement of atmospheric stability, $R^{33}$ is preferably a halogen atom.

In Formula (3), $Ch^{31}$ is a sulfur atom or a selenium atom. The preferable aspects of $Ch^{31}$ in Formula (3) are the same as that of $Ch^{11}$ in Formula (1).

$X^{11}$, $X^{12}$, $X^{13}$, and $X^{14}$ in Formula (3) are respectively the same as $X^{11}$, $X^{12}$, $X^{13}$, and $X^{14}$ in Formula (1), and the preferable aspects thereof are also the same.

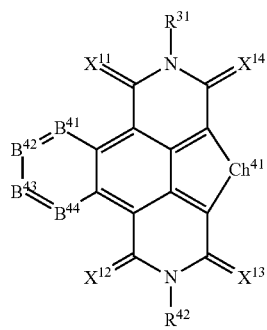

(4)

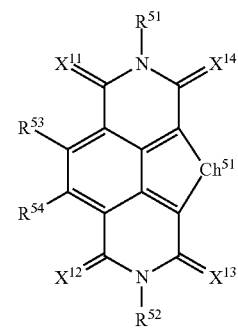

(5)

In Formula (4), $R^{41}$ and $R^{42}$ each independently represent a hydrogen atom, a linear, branched, or cyclic alkyl group having 1 to 20 carbon atoms, an aryl group having 6 to 20 carbon atoms, or a heteroaryl group having 3 to 20 carbon atoms. The preferable aspects of $R^{41}$ and $R^{42}$ are the same as that of $R^N$ in Formula (1).

In Formula (4), $B^{41}$, $B^{42}$, $B^{43}$, and $B^{44}$ (that is, $B^{41}$ to $B^{44}$) each independently represent —N= or —C($R^M$)=.

In view of improvement of the atmospheric stability, it is preferable that all of $B^{41}$ to $B^{44}$ are —C($R^M$)= (that is, a ring formed by $B^{41}$ to $B^{44}$ is a benzene ring).

The definition of $R^M$ in Formula (4) is the same as that of $R^M$ in Formula (1), and preferable aspects thereof are also the same. In Formula (4), in a case where a plurality of $R^M$'s exist, the plurality of $R^M$'s may be identical to or different from each other.

In a case where at least one of $B^{41}$ or $B^{44}$ in Formula (4) is —C($R^M$)=, it is preferable that at least one of $R^M$'s is a halogen atom, since the atmospheric stability is improved.

In Formula (4), $Ch^{41}$ is a sulfur atom or a selenium atom. The preferable aspects of $Ch^{41}$ are the same as that of $Ch^{11}$ in Formula (1).)

$X^{11}$, $X^{12}$, $X^{13}$, and $X^{14}$ in Formula (4) are respectively the same as $X^{11}$, $X^{12}$, $X^{13}$, and $X^{14}$ in Formula (1), and the preferable aspects thereof are also the same.

In Formula (5), $R^{51}$ and $R^{52}$ each independently represent a hydrogen atom, a linear, branched, or cyclic alkyl group having 1 to 20 carbon atoms, an aryl group having 6 to 20 carbon atoms, or a heteroaryl group having 3 to 20 carbon atoms. The preferable aspects of $R_{51}$ and $R_{52}$ in Formula (2) are the same as that of $R^N$ in Formula (1).

In Formula (5), $Ch^{51}$ is a sulfur atom or a selenium atom. The preferable aspects of $Ch^{51}$ are the same as that of $Ch^{11}$ in Formula (1).

$X^{11}$, $X^{12}$, $X^{13}$, and $X^{14}$ in Formula (5) are respectively the same as $X^{11}$, $X^{12}$, $X^{13}$, and $X^{14}$ in Formula (1), and the preferable aspects thereof are also the same.

In Formula (5), $R^{53}$ and $R^{54}$ each independently represent a hydrogen atom, a halogen atom, or a cyano group. In view of improvement of the atmospheric stability, it is preferable that at least one of $R^{53}$ or $R^{54}$ is a halogen atom.

Specific examples of the compound represented by Formula (1) are provided below.

In the above table, a numerical value on the right of each atom in the description in the table represents the number of the atoms. For example, "CH2C3F7" means a "$CH_2C_3F_7$" group. "*" indicates a bonding position.

TABLE 1

(5)

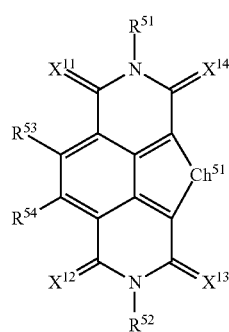

| No. | $Ch^{51}$ | $X^{11}$ | $X^{12}$ | $X^{13}$ | $X^{14}$ | $R^{53}$ | $R^{54}$ | $R^{51}$ | $R^{52}$ |
|---|---|---|---|---|---|---|---|---|---|
| 1 | S | O | O | O | O | H | H | H | H |
| 2 | S | O | O | O | O | H | H | —CH3 | —CH3 |
| 3 | S | O | O | O | O | H | H | -nC6H13 | -nC6H13 |
| 4 | S | O | O | O | O | H | H | *—⬡ | *—⬡ |

TABLE 1-continued (5)

| No. | Ch$^{51}$ | X$^{11}$ | X$^{12}$ | X$^{13}$ | X$^{14}$ | R$^{53}$ | R$^{54}$ | R$^{51}$ | R$^{52}$ |
|---|---|---|---|---|---|---|---|---|---|
| 5 | S | S | S | O | O | H | H | *-cyclohexyl | *-cyclohexyl |
| 6 | S | O | O | S | S | H | H | *-cyclohexyl | *-cyclohexyl |
| 7 | Se | O | S | S | O | H | H | *-cyclohexyl | *-cyclohexyl |
| 8 | S | O | O | O | O | H | H | —CH2C3F7 | —CH2C3F7 |
| 9 | S | O | O | O | O | H | H | -isoPropyl | -isoPropyl |
| 10 | S | O | O | O | O | H | H | -tert-Butyl | -tert-Butyl |

TABLE 2

| No. | Ch$^{51}$ | X$^{11}$ | X$^{12}$ | X$^{13}$ | X$^{14}$ | R$^{53}$ | R$^{54}$ | R$^{51}$ | R$^{52}$ |
|---|---|---|---|---|---|---|---|---|---|
| 11 | Se | S | S | O | O | H | H | *-CH(C8H17)(C8H17) | *-CH(C8H17)(C8H17) |
| 12 | S | O | O | O | O | H | H | *-CH(C8H17)(C8H17) | *-CH(C8H17)(C10H21) |
| 13 | S | O | O | O | O | H | H | —C2H4C5F11 | —C2H4C5F11 |
| 14 | S | O | O | O | O | Cl | H | *-cyclohexyl | *-cyclohexyl |
| 15 | S | O | O | O | O | F | H | *-phenyl | *-phenyl |
| 16 | S | O | O | O | O | F | F | *-mesityl (2,4,6-trimethylphenyl) | *-mesityl (2,4,6-trimethylphenyl) |
| 17 | S | O | O | O | O | CN | H | *-tert-Butyl | *-tert-Butyl |

TABLE 2-continued
| No. | $Ch^{51}$ | $X^{11}$ | $X^{12}$ | $X^{13}$ | $X^{14}$ | $R^{53}$ | $R^{54}$ | $R^{51}$ | $R^{52}$ |
|-----|-----------|----------|----------|----------|----------|----------|----------|----------|----------|
| 18 | SO2 | O | O | O | O | Br | H | 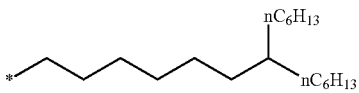 | 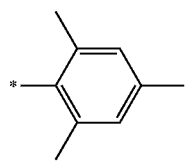 |
| 19 | S | O | O | O | O | NO2 | H | 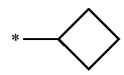 |  |
| 20 | SeO2 | O | O | O | O | CH3 | -nC6H13 | 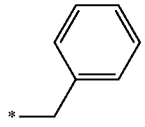 | 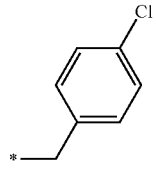 |
| 21 | S | O | O | O | O | —CO2CH3 | H | 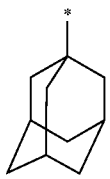 | 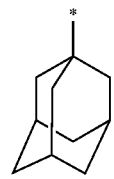 |
| 22 | S | O | O | O | O | H | —Ph | 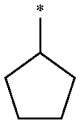 | 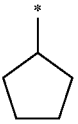 |
| 23 | S | O | O | O | O | —COOH | H | —CF3 | —C2F5 |
| 24 | S | O | O | O | O | H | —CF3 | 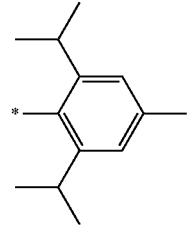 | 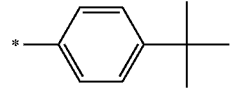 |
| 25 | SeO2 | O | O | O | O | —OCH3 | H | 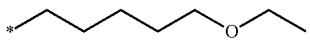 | 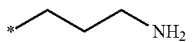 |

TABLE 3
(6)
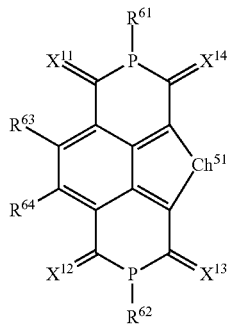
| No. | Ch⁶¹ | X¹¹ | X¹² | X¹³ | X¹⁴ | R⁶³ | R⁶⁴ | R⁶¹ | R⁶² |
|---|---|---|---|---|---|---|---|---|---|
| 26 | S | O | O | O | O | H | H | H | H |
| 27 | S | O | O | O | O | H | H | —CH3 | —CH3 |
| 28 | S | O | O | O | O | H | H | *(pent-4-enyl) | -nC6H13 |
| 29 | S | O | O | O | O | H | H | *-cyclohexyl | *-cyclohexyl |
| 30 | S | S | S | O | O | H | H | -nC10H21 | -nC10H21 |
| 31 | S | O | O | S | S | H | H | *-cyclohexyl | *-cyclohexyl |
| 32 | Se | O | S | S | O | H | H | *-tetrahydropyran-2-yl | *-tetrahydropyran-2-yl |
| 33 | SeO | O | O | O | O | *-thiophen-2-yl | *-thiophen-2-yl | *-(CH2)3-OC(O)C(CH3)=CH2 | —CH2C3F7 |
| 34 | SO | O | O | O | O | *-furan-3-yl | *-isothiazol-3-yl | -isoPropyl | -isoPropyl |
| 35 | SO2 | O | O | O | O | H | H | *-(CH2)4-OH | *-(CH2)4-SO3H |

TABLE 4
(3)
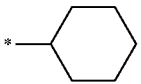
| No. | Ch³¹ | X¹¹ | X¹² | X¹³ | X¹⁴ | R³³ | R³¹ | R³² |
|-----|------|-----|-----|-----|-----|-----|-----|-----|
| 36 | S | O | O | O | O | H | H | H |
| 37 | S | O | O | O | O | H | —CH3 | —CH3 |
| 38 | S | O | O | O | O | Cl | -nC6H13 | -nC6H13 |
| 39 | S | O | O | O | O | F |  | 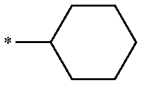 |
| 40 | S | S | S | O | O | CN |  | 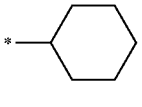 |
| 41 | S | O | O | S | S | —N(CH3)2 |  | 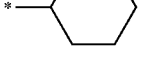 |
| 42 | Se | O | S | S | O | H |  | 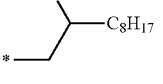 |
| 43 | S | O | O | O | O | H | —CH2C3F7 | —CH2C3F7 |
| 44 | S | O | O | O | O | H | -isoPropyl | -isoPropyl |
| 45 | S | O | O | O | O | H | -tert-Butyl | -tert-Butyl |
TABLE 5
| No. | Ch³¹ | X¹¹ | X¹² | X¹³ | X¹⁴ | R³³ | R³¹ | R³² |
|-----|------|-----|-----|-----|-----|-----|-----|-----|
| 46 | Se | S | S | O | O | H | 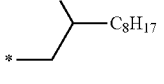 | 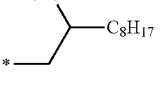 |
| 47 | S | O | O | O | O | H | 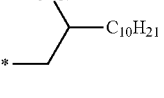 | 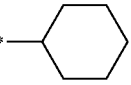 |
| 48 | S | O | O | O | O | H | —C22H4C5F11 | —C2H4C5F11 |
| 49 | S | O | O | O | O | Cl | 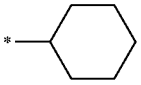 | 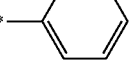 |
| 50 | S | O | O | O | O | F | 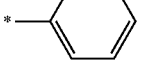 | |

TABLE 5-continued
| No. | Ch³¹ | X¹¹ | X¹² | X¹³ | X¹⁴ | R³³ | R³¹ | R³² |
|---|---|---|---|---|---|---|---|---|
| 51 | S | O | O | O | O | F | 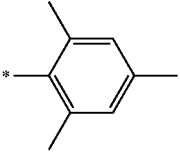 | 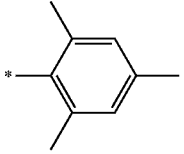 |
| 52 | S | O | O | O | O | CN |  |  |
| 53 | SO2 | O | O | O | O | Br | 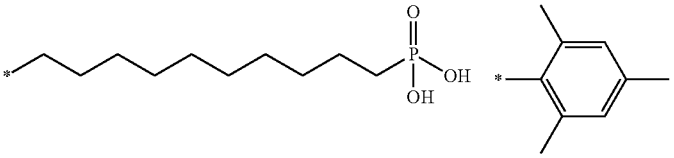 | 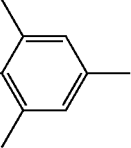 |
| 54 | S | O | O | O | O | NO2 | 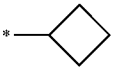 |  |
| 55 | SeO2 | O | O | O | O | CH3 | 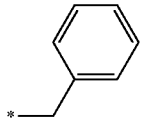 | 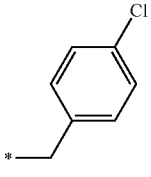 |
| 56 | S | O | O | O | O | —CO2CH3 | 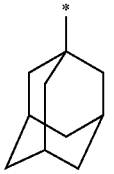 | 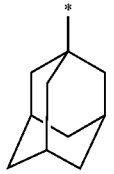 |
| 57 | S | O | O | O | O | H | 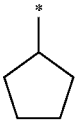 | 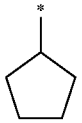 |
| 58 | S | O | O | O | O | —COOH | —CF3 | —C2F5 |

TABLE 5-continued
| No. | Ch³¹ | X¹¹ | X¹² | X¹³ | X¹⁴ | R³³ | R³¹ | R³² |
|---|---|---|---|---|---|---|---|---|
| 59 | SO | O | O | O | O | H | 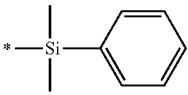 | 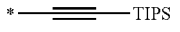 —TIPS |
| 60 | SeO2 | O | O | O | O | —OCH3 | 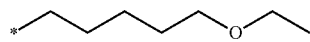 | 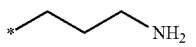 |
TABLE 6
(7)
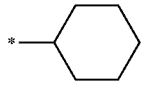
| No. | Ch⁷¹ | X¹¹ | X¹² | X¹³ | X¹⁴ | R⁷¹ | R⁷² |
|---|---|---|---|---|---|---|---|
| 61 | S | O | O | O | O | H | H |
| 62 | S | O | O | O | O | —CH3 | —CH3 |
| 63 | S | O | O | O | O | -nC6H13 | -nC6H13 |
| 64 | S | O | O | O | O | 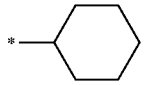 | 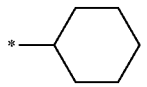 |
| 65 | S | S | S | O | O | -nC13H27 | -nC20H41 |
| 66 | S | O | O | S | S | 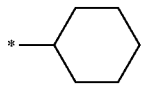 | 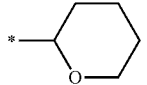 |
| 67 | Se | O | S | S | O | 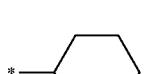 | 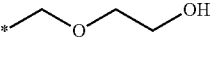 |
| 68 | SeO | O | O | O | O | 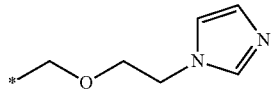 | 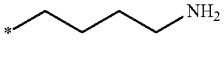 |
| 69 | SO | O | O | O | O | 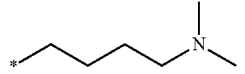 | 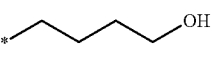 |
| 70 | SO₂ | O | O | O | O | 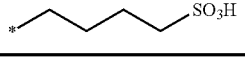 OH | 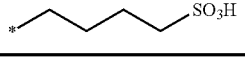 SO₃H |

-continued
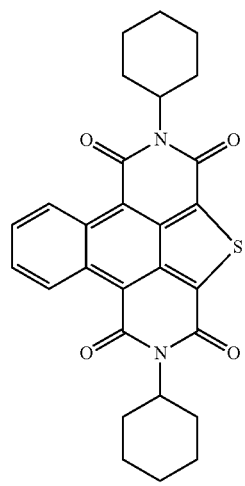 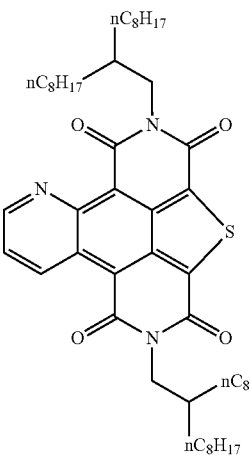 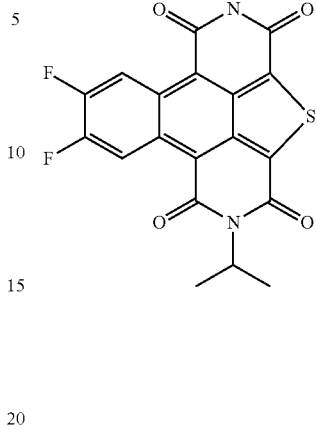 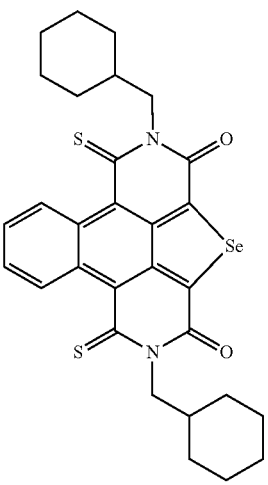
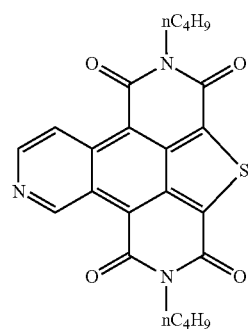 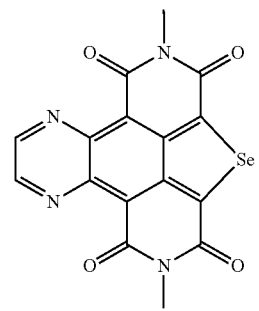 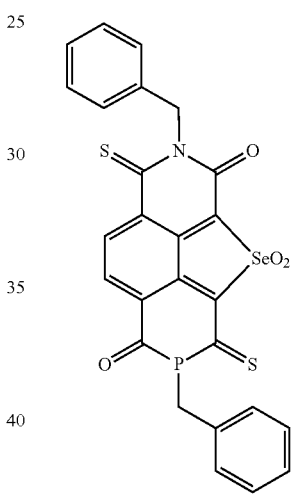 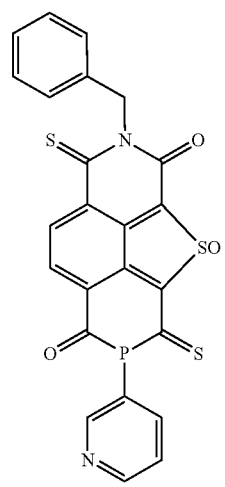
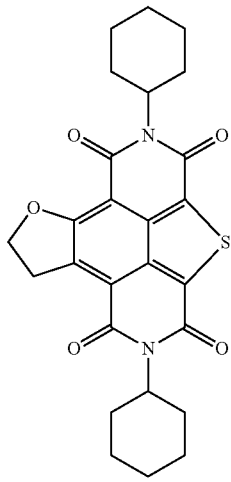 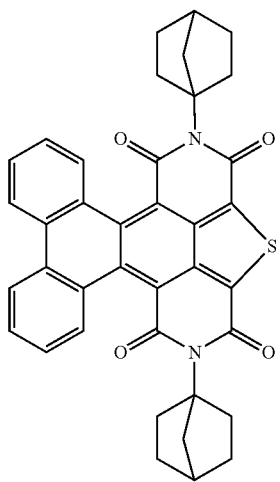 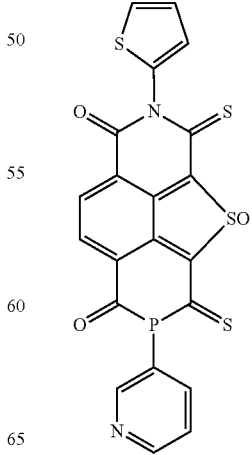 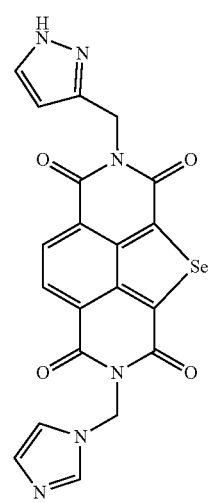

23

-continued

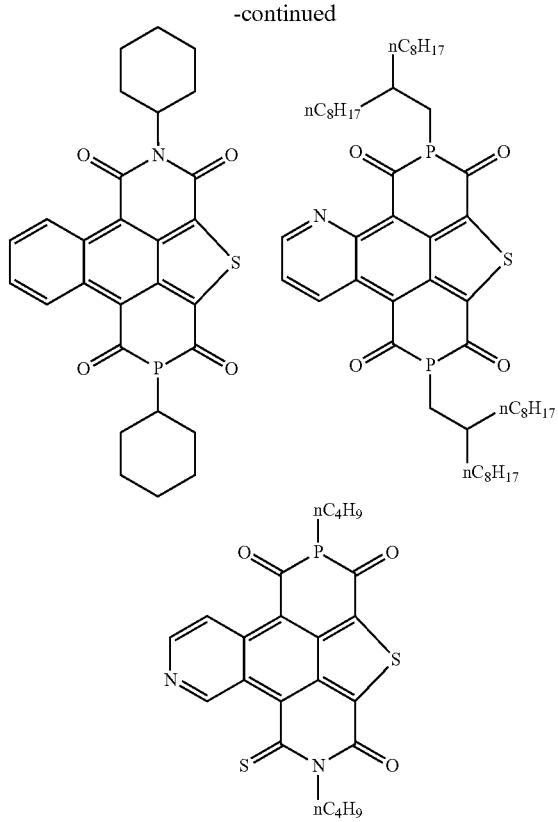

<Method of Manufacturing Compound Represented by Formula (1)>

A method of manufacturing the compound represented by Formula (1) is not particularly limited, and can be manufactured with reference to well-known methods. Specifically, the compound represented by Formula (1) can be manufactured by the method corresponding to the example described below.

<Compound Represented by Formula (2)>

The compound represented by Formula (2) is a novel compound, and can be suitably used in an organic semiconductor film of an organic thin film transistor, and also can be used in other applications described below.

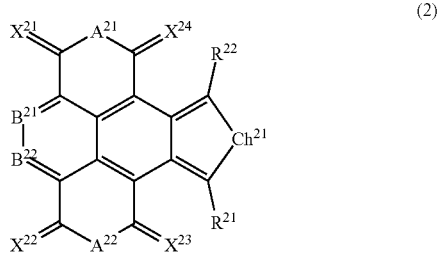

$A^{21}$ and $A^{22}$ in Formula (2) are the same as $A^{11}$ and $A^{12}$ in Formula (1) and each independently represent —N(RN)—, —P(RN)—, or —O—. $R^N$ represents a hydrogen atom or a substituent. A plurality of $R^N$'s are identical to or different from each other.

The preferable aspects of $A^{21}$ and $A^{22}$ in Formula (2) are the same as those of $A^{11}$ and $A^{12}$ in Formula (1).

$B^{21}$ and $B^{22}$ in Formula (2) are the same as $B^{11}$ and $B^{12}$ in Formula (1) and each independently represent —N= or —C($R^M$)=. $R^M$ represents a hydrogen atom or a substituent. In Formula (2), in a case where a plurality of $R^M$'s exist, the plurality of $R^M$'s may be identical to or different from each other.

The preferable aspects of $B^{21}$ and $B^{22}$ in Formula (2) are the same as those of $B^{11}$ and $B^{12}$ in Formula (1).

In a case where both of $B^{21}$ and $B^{22}$ are —C($R^M$)=, $R^M$ included in $B^{21}$ and $R^M$ included in $B^{22}$ may form a ring. The aspect in this case is also the same as in Formula (1).

$X^{21}$, $X^{22}$, $X^{23}$, and $X^{24}$ in Formula (2) are respectively the same as $X^{11}$, $X^{12}$, $X^{13}$, and $X^{14}$ in Formula (1), and the preferable aspects thereof are also the same, and each independently represent an oxygen atom or a sulfur atom.

Preferable aspects of $X^{21}$, $X^{22}$, $X^{23}$, and $X^{24}$ in Formula (2) are the same as those of $X^{11}$, $X^{12}$, $X^{13}$, and $X^{14}$ in Formula (1).

$Ch^{21}$ in Formula (2) has the same meaning as $Ch^{11}$ in Formula (1), and represents a sulfur atom, a sulfinyl group, a sulfonyl group, a selenium atom, a seleninyl group, or a selenonyl group.

The preferable aspects of $Ch^{21}$ in Formula (2) are the same as that of $Ch^{11}$ in Formula (1).

In Formula (2), $R^{21}$ and $R^{22}$ each independently represent a hydrogen atom or s substituent. The definition of the substituent is as described above.

Among these, in view of improvement of carrier mobility, $R^{21}$ and $R^{22}$ each independently and preferably represent a hydrogen atom, a cyano group, a halogen atom, a silyl group, or a linear, branched, or cyclic alkyl group having 1 to 20 carbon atoms and more preferably represent a hydrogen atom, a methyl group, a halogen atom, or a cyano group.

Specific examples of the compound represented by Formula (2) are provided below.

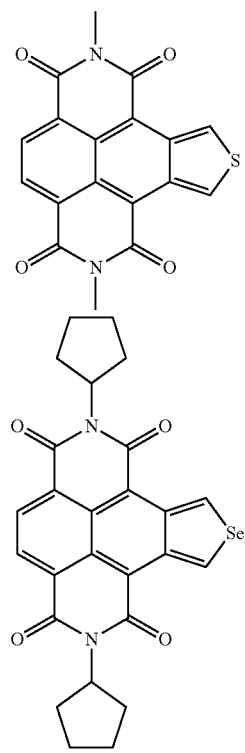

-continued

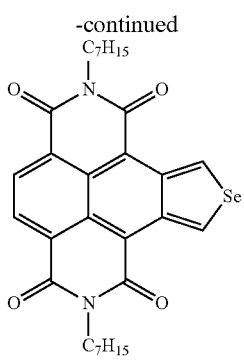

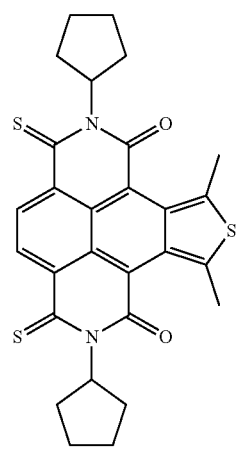

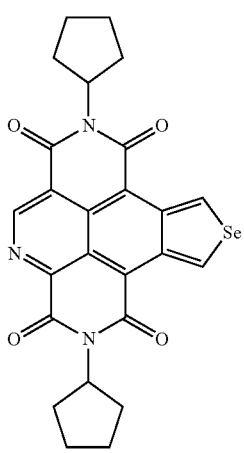

-continued

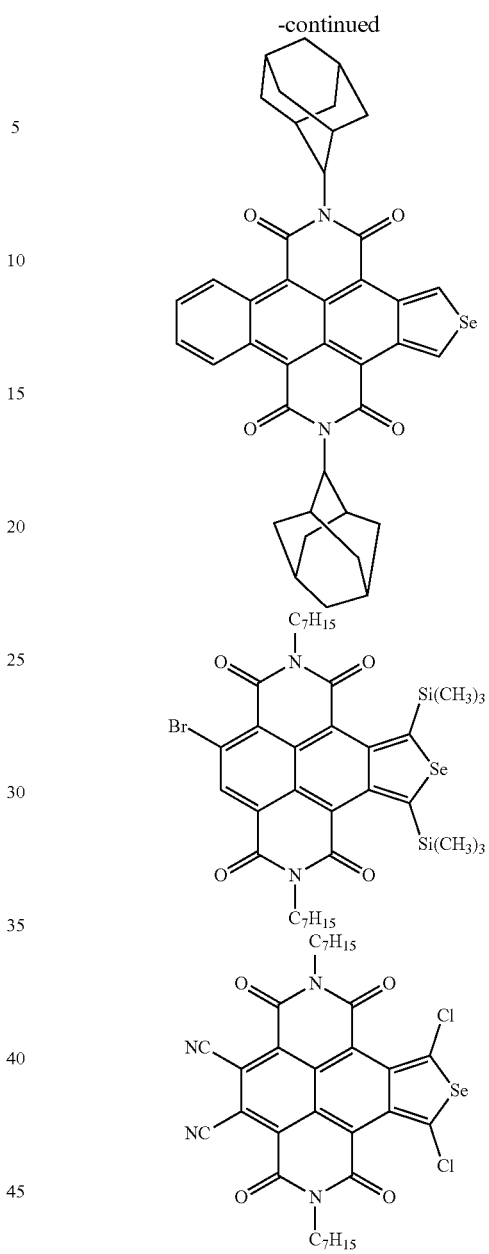

<Method of Manufacturing Compound Represented by Formula (2)>

The method of manufacturing the compound represented by Formula (2) is not compound limited, and the compound represented by Formula (2) can be manufactured with reference to well-known methods.

<Structure of Organic Thin Film Transistor and Method of Manufacturing Organic Thin Film Transistor>

Subsequently, a structure of the organic thin film transistor according to the present invention in which the compound represented by Formulae (1) and (2) is used in the organic semiconductor film of the organic thin film transistor and a manufacturing method thereof are described.

The organic thin film transistor according to the present invention may have an organic semiconductor film (organic semiconductor layer) including a compound represented by Formulae (1) and (2) and may further have a source electrode, a drain electrode, and a gate electrode.

The structure of the organic thin film transistor according to the present embodiment is not particularly limited. For example, the structure thereof may have any one of a bottom contact type (bottom contact-bottom gate type and bottom contact-top gate type) and top contact type (top contact-bottom gate type and top contact-top gate type).

Hereinafter, an example of the organic thin film transistor according to the present invention is described with reference to the drawings.

FIG. 1 is a cross-sectional view schematically illustrating a bottom contact type organic thin film transistor 100 according to one embodiment of the present invention.

In the example of FIG. 1, the organic thin film transistor 100 has a substrate 10, a gate electrode 20, a gate insulating film 30, a source electrode 40, a drain electrode 42, an organic semiconductor film (organic semiconductor layer) 50, and a sealing layer 60. Here, the organic semiconductor film 50 is manufactured by using the compound represented by Formula (1) or (2).

Hereinafter, each of methods of manufacturing the substrate, the gate electrode, the gate insulating film, the source electrode, the drain electrode, the organic semiconductor film (the organic semiconductor layer), and the sealing layer is specifically described below.

(Substrate)

The substrate plays a role of supporting the gate electrode, the source electrode, the drain electrode, and the like which will be described later.

The type of the substrate is not particularly limited, and examples thereof include a plastic substrate, a glass substrate, and a ceramic substrate. Among these, in view of applicability to each device and costs, a glass substrate or a plastic substrate is preferable.

(Gate Electrode)

Examples of materials of the gate electrode include metal such as gold (Au), silver, aluminum, copper, chromium, nickel, cobalt, titanium, platinum, magnesium, calcium, barium, or sodium; conductive oxide such as $InO_2$, $SnO_2$, or indium tin oxide (ITO); a conductive polymer such as polyaniline, polypyrrole, polythiophene, polyacetylene, or polydiacetylene; a semiconductor such as silicon, germanium, or gallium arsenide; and a carbon material such as fullerene, carbon nanotubes, or graphite. Among these, a metal is preferable, and silver and aluminum are more preferable.

The thickness of the gate electrode is not particularly limited but is preferably 20 to 200 nm.

The gate electrode may function as a substrate, and, in this case, the substrate may not be provided.

A method of forming the gate electrode is not particularly limited, but examples thereof include a method of vacuum vapor-depositing or sputtering an electrode material onto a substrate, a method of coating a substrate with a composition for forming an electrode, a method of printing a composition for forming an electrode onto a substrate, and the like. Examples of a patterning method in a case where the electrode is patterned include a photolithography method; a printing method such as ink jet printing, screen printing, offset printing, or relief printing (flexo printing); and a mask vapor deposition method.

(Gate Insulating Film)

Examples of the material of the gate insulating film include a polymer such as polymethyl methacrylate, polystyrene, polyvinyl phenol, polyimide, polycarbonate, polyester, polyvinyl alcohol, polyvinyl acetate, polyurethane, polysulfone, polybenzoxazole, polysilsesquioxane, an epoxy resin, and a phenol resin; oxide such as silicon dioxide, aluminum oxide, and titanium oxide; and nitride such as silicon nitride. Among these materials, in view of the compatibility with the organic semiconductor film, it is preferable that the material of the gate insulating film is a polymer.

The film thickness of the gate insulating film is not particularly limited but is preferably 100 to 1,000 nm.

The method of forming the gate insulating film is not particularly limited, and examples thereof include a method of coating a substrate on which a gate electrode is formed with a composition for forming a gate insulating film and a method of evaporating or sputtering a material of a gate insulating film.

(Source Electrode and Drain Electrode)

Specific examples of the materials of the source electrode and the drain electrode are the same as those of the gate electrode. Among these, a metal is preferable, and silver is more preferable.

The method of forming a source electrode and a drain electrode is not particularly limited, and examples thereof include a method of vacuum-evaporating or sputtering an electrode material on a substrate on which a gate electrode and a gate insulating film are formed and a method of applying or printing an electrode forming composition. Specific examples of the patterning method are the same as those of the gate electrode.

(Organic Semiconductor Film)

The method of manufacturing an organic semiconductor film is not particularly limited, as long as the organic semiconductor film including the compound represented by Formula (1) or (2) is manufactured. However, for example, the organic semiconductor film can be manufactured by coating a substrate with an organic thin film transistor composition (described below) including the compound represented by Formula (1) or (2) and drying the organic thin film transistor composition.

The expression "coating a substrate with an organic thin film transistor composition" includes an aspect of applying the organic thin film transistor composition over the substrate through an independent layer provided on the substrate, in addition to an aspect of directly applying the organic thin film transistor composition to the substrate.

Well-known methods can be used as the coating method with the organic thin film transistor composition, and examples thereof include a bar coating method, a spin coating method, a knife coating method, a doctor blade method, an ink jet printing method, a flexographic printing method, a gravure printing method, and a screen printing method. As the coating method with the organic thin film transistor composition, a method (so-called gap cast method) of forming an organic semiconductor film disclosed in JP2013-207085A and a method (a so-called edge casting method and a continuous edge casting method) of manufacturing an organic semiconductor thin film disclosed in WO2014/175351A and the like are suitably used.

With respect to drying (a drying treatment), an optimum condition may be suitably selected depending on the types of the respective components included in the organic thin film transistor composition so as to perform natural drying. However, in view of improvement of productivity, a heating treatment is preferably performed. For example, the heating temperature is preferably 30° C. to 150° C. and more preferably 40° C. to 120° C., and the heating time is preferably 10 to 300 minutes and more preferably 20 to 180 minutes.

The film thickness of the manufactured organic semiconductor film is not particularly limited. However, in view of the excellent effect of the present invention, the film thickness is preferably 10 to 500 nm and more preferably 30 to 200 nm.

In this manner, the organic semiconductor film containing the compound represented by Formula (1) or (2) is suitably used in the organic thin film transistor. However, the present invention is not limited to this application, and the organic semiconductor film containing the compound represented by Formula (1) or (2) can be applied to other applications described below.

(Sealing Layer)

In view of durability, the organic thin film of the present invention preferably includes a sealing layer as an outermost layer. In the sealing layer, a known sealant (sealing layer forming composition) can be used.

The thickness of the sealing layer is not particularly limited, and is preferably 0.2 to 10 µm.

(Other Organic Thin Film Transistors)

Figure 2:
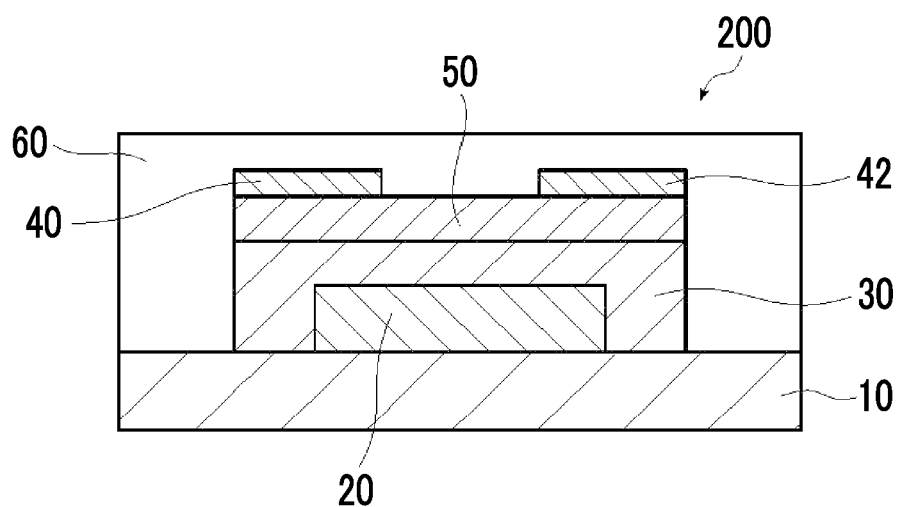
FIG. 2 is a cross-sectional view schematically illustrating a top contact type organic thin film transistor according to one embodiment of the present invention.

FIG. 2 is a cross-sectional view schematically illustrating a top contact type organic thin film transistor 200 according to one embodiment of the present invention.

In the example of FIG. 2, the organic thin film transistor 200 has the substrate 10, the gate electrode 20, the gate insulating film 30, the source electrode 40, the drain electrode 42, the organic semiconductor film (organic semiconductor layer) 50, and the sealing layer 60. Here, the organic semiconductor film 50 is formed by using the organic thin film transistor composition according to the present invention described below.

The substrate, the gate electrode, the gate insulating film, the source electrode, the drain electrode, the organic semiconductor film, and the sealing layer are as described above, and the description thereof is omitted.

(Application of Organic Thin Film Transistor)

The above organic thin film transistor can be applied to a display unit of electronic paper and a display device, which displays an image. Electronic paper and a display device may have well-known structures, and thus the description thereof is omitted.

[Organic Thin Film Transistor Composition]

The organic thin film transistor composition according to the present invention is used in the manufacturing of the organic semiconductor film of the organic thin film transistor.

The organic thin film transistor composition described below may be used in the other uses described below. In this case, the "organic thin film transistor composition" may be simply referred to as an "organic semiconductor composition".

The organic thin film transistor composition contains the compound represented by Formula (1) or (2). However, generally, in view of the improvement of the coating properties thereof, the organic thin film transistor composition further contains an organic solvent.

In a case where the organic thin film transistor composition contains an organic solvent, the content of the compound represented by Formula (1) or (2) is preferably 0.01 to 20 mass %, more preferably 0.1 to 10 mass %, and even more preferably 0.5 to 5 mass % with respect to the total mass of the organic thin film transistor composition.

<Organic Solvent>

The organic solvent is not particularly limited, and examples thereof include a hydrocarbon solvent such as hexane, octane, and decane, an aromatic hydrocarbon solvent such as toluene, xylene, mesitylene, ethylbenzene, decalin, 1-methylnaphthalene, tetralin, and anisole, a ketone solvent such as acetone, methyl ethyl ketone, methyl isobutyl ketone, and cyclohexanone, a halogenated hydrocarbon solvent such as dichloromethane, chloroform, tetrachloromethane, dichloroethane, trichloroethane, tetrachloroethane, chlorobenzene, dichlorobenzene, and chlorotoluene, an ester solvent such as ethyl acetate, butyl acetate, amyl acetate, and ethyl lactate, an alcohol solvent such as methanol, propanol, butanol, pentanol, hexanol, cyclohexanol, methyl cellosolve, ethyl cellosolve, and ethylene glycol, an ether solvent such as butoxybenzene, dibutyl ether, tetrahydrofuran, and dioxane, an amide solvent such as N,N-dimethylformamide and N,N-dimethylacetamide, an imide solvent such as 1-methyl-2-pyrrolidone and 1-methyl-2-imidazolidinone, a sulfoxide type solvent such as dimethylsulfoxide, and a nitrile solvent such as acetonitrile.

Among these, in view of excellent solubility of the compound represented by Formula (1) or (2), an aromatic hydrocarbon-based solvent is preferably used.

The organic solvent may be used singly or two or more kinds thereof may be used in combination.

In a case where the organic solvent is contained, the content thereof is preferably 90 to 99.99 mass %, more preferably 95 to 99.99 mass %, even more preferably 96 to 99.95 mass %, with respect to the total mass of the organic thin film transistor composition.

<Binder Polymer>

The organic thin film transistor composition may further contain a binder polymer.

The types of the binder polymer are not particularly limited, and well-known binder polymers can be used. Examples thereof include a polymer compound such as a polystyrene resin, an acrylic resin, rubber, and a thermoplastic elastomer.

Among these, as the binder polymer, a polymer compound (a polymer having a monomer unit having a benzene ring group) having a benzene ring is preferable. The content of the monomer unit having a benzene ring is not particularly limited. However, the content is preferably 50 mol % or greater, more preferably 70 mol % or greater, and even more preferably 90 mol % or greater with respect to the total monomer unit. The upper limit thereof is not particularly limited, and examples thereof include 100 mol %.

Specific examples of the binder polymer include polystyrene, poly(α-methylstyrene), polyvinyl cinnamate, poly(4-vinylphenyl), and poly(4-methylstyrene).

The weight-average molecular weight of the binder polymer is not particularly limited, but is preferably 1,000 to 2,000,000, more preferably 3,000 to 1,000,000, and still more preferably 5,000 to 600,000. The weight-average molecular weight can be obtained by gel permeation chromatography (GPC).

The content in a case where the binder polymer is contained is preferably 1 to 50 parts by mass, and more preferably 5 to 30 parts by mass with respect to 100 parts by mass of the compound represented by Formula (1) or (2) included in the organic thin film transistor composition.

<Other Components>

The organic thin film transistor composition may further contain other components in addition to the above. Examples of the other component include a surfactant and a phenolic reducing agent (a so-called migration inhibitor).

In addition to these components, components included in the organic thin film transistor composition (organic semiconductor composition) in the related art may be contained.

<Preparation Method>

The method of preparing the organic thin film transistor is not particularly limited, and well-known methods can be employed. For example, the organic thin film transistor composition according to the present invention can be obtained by adding the compound represented by Formula (1) or (2) in the predetermined amount in the organic solvent and suitably performing a stirring treatment.

[Organic Thin Film Transistor Material]

An organic thin film transistor material according to the present invention contains the compound represented by Formula (1) or (2). The organic thin film transistor material is used in the organic thin film transistor and refers to a material exhibiting semiconductor characteristics.

The compound represented by Formula (1) or (2) is a material exhibiting properties as a semiconductor and is an n-type (electron transporting type) organic semiconductor material which conducts electrons as carriers.

The organic thin film transistor material may be used in the other applications described below. In this case, the "organic thin film transistor material" may be simply referred to as an "organic semiconductor material".

[Other Applications of Compound Represented by Formulae (1) and (2)]

The compound represented by Formulae (1) and (2) has excellent properties as described above and thus can be suitably used in other applications in addition to the organic thin film transistor.

Examples of the other applications include a non-luminous organic semiconductor device. The non-luminous organic semiconductor device means a device that is not intended to emit light.

In addition to the organic thin film transistor described above, examples of the non-luminous organic semiconductor device include an organic photoelectric conversion element (individual imaging element for optical sensor application, solar cell for energy conversion, and the like), a gas sensor, an organic rectifying element, an organic inverter, and an information recording element.

The non-luminous organic semiconductor device preferably causes the organic semiconductor film to function as an electronic element. The organic semiconductor film includes an organic semiconductor film including the compound represented by Formula (1) or (2).

EXAMPLES

Hereinafter, the organic thin film transistor according to the present invention is specifically described with reference to examples. However, the present invention is not limited thereto.

Example Compounds 1 to 3

Example Compounds 1 to 3 were synthesized in the following method.

Compound 3: Synthesis of $N^1,N^1,N^3,N^3$-tetramethylbenzo[c]thiophene-1,3-dicarboxamide

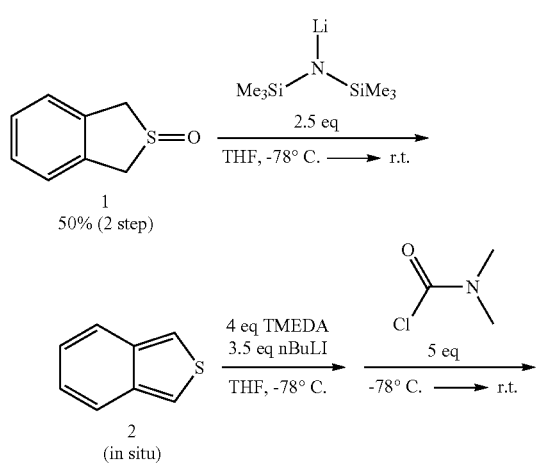

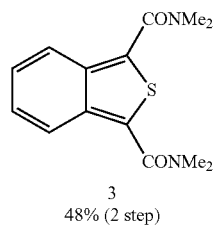

3
48% (2 step)

63.2 mL of a 1.3 mol/L THF solution of lithium bis(trimethylsilyl) amide was added to 500 mL of a tetrahydrofuran (THF) solution of 1,3-dihydrobenzo[c]thiophene-2-oxide (compound "1") (5.00 g, 32.8 mmol) under an argon atmosphere at −78° C., the temperature was returned to room temperature, and the solution was stirred for 30 minutes. A portion of the reaction solution was quenching with water, the organic layer was extracted and washed with ethyl acetate and saline, concentration was performed under reduced pressure, and the generation of benzo[c]thiophene (Compound "2") was checked by Nuclear Magnetic Resonance (NMR). This reaction solution was used for the subsequent reaction without change.

The reaction solution was cooled to −78° C. under an argon atmosphere, N,N,N',N'-tetramethylene diamine (19.6 mL, 131 mmol) was added, a 1.6 mol/L THF solution of n-butyl lithium (71.8 mL, 115 mmol) was added dropwise, and the solution was stirred for 30 minutes. After stirring, dimethylcarbamoyl chloride (15.0 mL, 164 mmol) was added dropwise, and the mixture was further stirred for 30 minutes. The temperature of the reaction solution was returned to room temperature, and water was added so as to stop the reaction. The organic layer was extracted and washed with ethyl acetate and saline, and concentration was performed under reduced pressure. The concentrated residue was purified by silica gel column chromatography (CHCl$_3$: acetone=10:1), so as to obtain Compound "3" (4.30 g, 15.6 mmol, 48% yield for 2 steps) as a pale yellow solid.

Compound 1 (1,3-dihydrobenzo[c]thiophene-2-oxide) was synthesized with reference to the description in Journal of Materials Chemistry, 2012, vol. 22, #44, p. 23514 to 23524.

$^1$H-NMR (CDCl$_3$, 400 MHz) δ: 7.64-7.58 (m, 2H), 7.21-7.15 (m, 2H), 3.16 (s, 12H); $^{13}$H-NMR (CDCl$_3$, 400 MHz) δ: 164.69 136.74, 128.55, 125.65, 121.55, 37.99.

Compound 4: Synthesis of 4,7-dibromo-$N^1,N^1,N^3,N^3$-tetramethylbenzo[c]thiophene-1,3-dicarboxamide

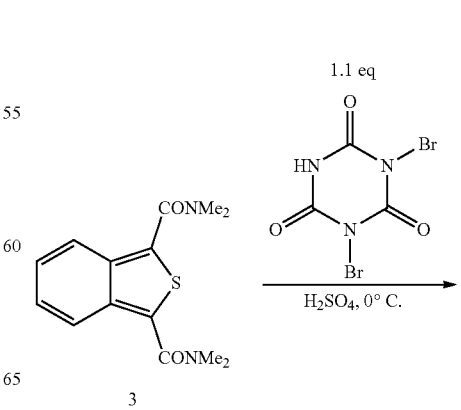

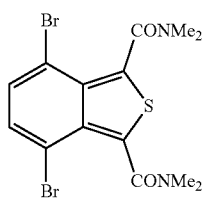

4
83%

Dibromoisocyanuric acid (2.61 g, 9.11 mmol) was added to a 120 mL of concentrated sulfuric acid solution of Compound "3" (2.40 g, 8.68 mmol) at 0° C., and the mixture was stirred for 30 minutes. Thereafter, the reaction solution was poured into 500 mL of ice water to stop the reaction. The organic layer was extracted and washed with ethyl acetate and saline, and concentration was performed under reduced pressure. The concentrated residue was purified by silica gel column chromatography (hexane:acetone=1:1), so as to obtain Compound "4" (3.13 g, 7.21 mmol, 83% yield) as a pale yellow solid.

$^1$H-NMR (DMSO-d6, 400 MHz) δ: 7.40 (s, 2H), 3.06 (s, 6H), 2.78 (s, 6H)

Compound 5: Synthesis of 4,7-dicyano-N$^1$,N$^1$,N$^3$,N$^3$-tetramethylbenzo[c]thiophene-1,3-dicarboxamide

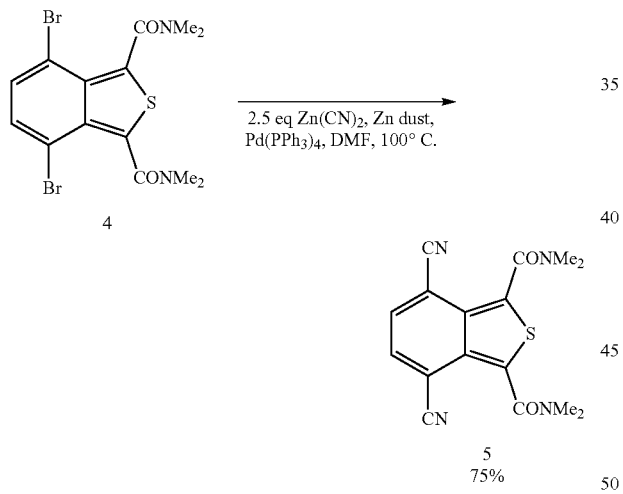

4

2.5 eq Zn(CN)$_2$, Zn dust,
Pd(PPh$_3$)$_4$, DMF, 100° C.

5
75%

Compound "4" (2.00 g, 4.61 mmol), zinc cyanide (II) (1.35 g, 11.5 mmol), tetrakis(triphenylphosphine) palladium (0) (267 mg, 0.231 mmol), zinc powder (30 mg, 0.461 mmol), and 53.6 mL of dimethylformamide were introduced to a Schlenk tube, and degassing and argon gas replacement were performed. The reaction solution was heated to 100° C., and stirring was performed for 12 hours. The temperature was cooled to the room temperature, and the reaction solution was added to water. The organic layer was extracted and washed with ethyl acetate and saline, and concentration was performed under reduced pressure. The concentrated residue was purified by silica gel column chromatography (hexane:CHCl$_3$:methanol=10:10:1), so as to obtain Compound "5" (1.07 g, 3.45 mmol, 75% yield) as a pale yellow solid.

$^1$H-NMR (DMSO-d$_6$, 400 MHz) δ: 7.40 (s, 2H), 3.06 (s, 6H), 2.78 (s, 6H); $^{13}$H-NMR (DMSO-d$_6$, 400 MHz) δ: 161.45, 132.28, 131.26, 130.17, 115.20, 109.63, 39.44, 35.62.

Compound 6: Synthesis of thieno[2,3,4,5-lmn][3,8]phenanthroline-1,3,5,7(2H,6H)-tetraone

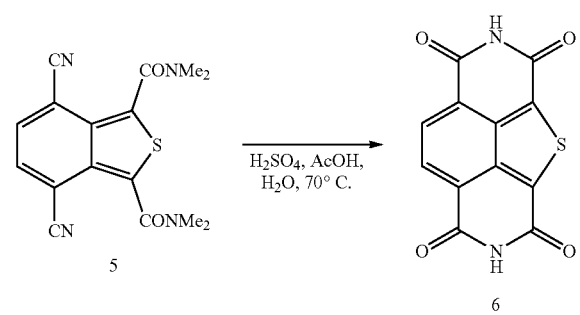

H$_2$SO$_4$, AcOH, H$_2$O, 70° C.

5

6

At room temperature, Compound "5" (340 mg, 1.04 mmol) was added to a mixed solvent of acetic acid (2.72 mL) and water (1.16 mL), and 0.68 ml of concentrated sulfuric acid was further added dropwise. The reaction solution was heated to 70° C., and stirring was performed for three hours. After the temperature was cooled to room temperature, the precipitate was filtered and washed with water and ethyl acetate, to obtain Compound "6" (210 mg, 0.23 mmol, 74% yield) as a yellow powder.

$^1$H-NMR (DMSO-d$_6$, 400 MHz) δ: 11.84 (s, 2H), 8.28 (brs, 6H);

HR-APCI Mass: calcd for M 271.9892, found (m/z) 272.9961 [M+H]+.

Example Compound 1: Synthesis of 2,6-dicyclohexylthieno[2,3,4,5-lmn][3,8]phenanthroline-1,3,5,7(2H,6H)-tetraone

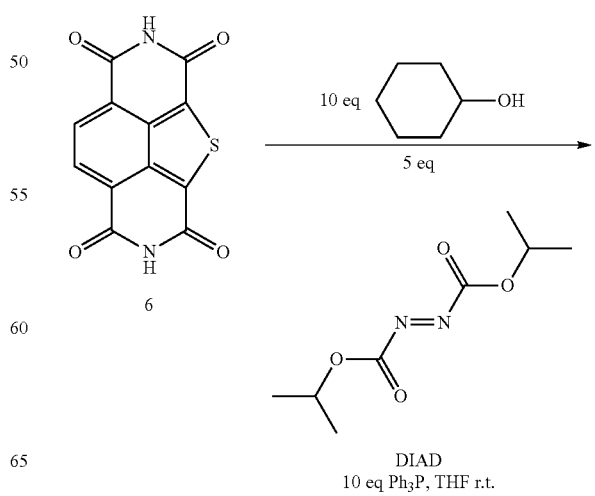

6

10 eq cyclohexanol
5 eq

DIAD
10 eq Ph$_3$P, THF r.t.

-continued

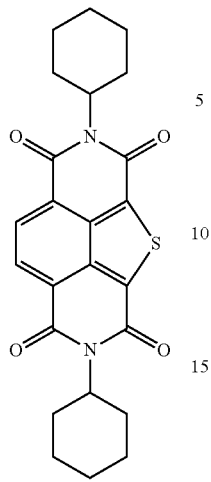

Example Compound 1

Compound "6" (100 mg, 0.367 mmol), cyclohexanol (0.391 mL, 3.67 mmol), triphenylphosphine (963 mg, 3.687 mmol), 10 mL of THF were added to the reaction vessel, the temperature was cooled to 0° C. under an argon atmosphere, and diisopropyl azodicarboxylate (0.356 mL, 1.84 mmol) was added dropwise. Then, the temperature of the reaction solution was returned to room temperature and the reaction solution was stirred for three hours. Thereafter, 10 mL of diluted hydrochloric acid was added to the reaction solution to stop the reaction. The organic layer was extracted and washed with ethyl acetate and saline, and concentration was performed under reduced pressure. A concentrated residue was purified by silica gel column chromatography (hexane:CHCl$_3$=1:1), gel permeation chromatography (GPC), and recrystallization (methanol/CHCl$_3$), so as to obtain Example Compound 1 (58 mg, 0.133 mmol, 36% yield), as a yellow powder.

$^1$H-NMR (CDCl$_3$ 400 MHz) δ: 8.30 (s, 2H), 4.97 (tt, J=12.4 and 3.6 Hz, 2H), 2.49 (qd, J=12.4 and 3.6 Hz, 4H), 1.90 (br d, J=13.2 HZ, 4H), 1.72 (br d, J=12.4 HZ, 6H), 1.50-1.23 (m, 6H); $^{13}$H-NMR (DMSO-d$_6$, 400 MHz) δ: 163.27, 159.96, 135.89, 130.76, 124.32, 54.70, 29.29, 26.68, 25.44.

Example Compound 2: Synthesis of 2,6-didecylthieno[2,3,4,5-lmn][3,8]phenanthroline-1,3,5,7(2H,6H)-tetraone -continued

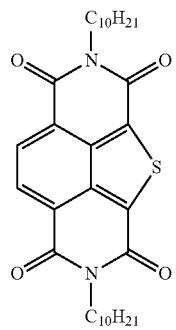

Example Compound 2

Compound "6" (250 mg, 0.918 mmol), normal decanol (1.14 mL, 9.18 mmol), triphenylphosphine (1.20 g, 4.59 mmol), and 25 mL of THF were added to the reaction vessel, the temperature was cooled to 0° C. under an argon atmosphere, and diisopropyl azodicarboxylate (0.533 mL, 2.75 mmol) was added dropwise. Then, the temperature of the reaction solution was returned to room temperature and the reaction solution was stirred for one hour. Thereafter, 10 mL of diluted hydrochloric acid was added to the reaction solution to stop the reaction. The organic layer was extracted and washed with ethyl acetate and saline, and concentration was performed under reduced pressure. A concentrated residue was purified by silica gel column chromatography (toluene), gel permeation chromatography (GPC), and recrystallization (methanol/CHCl$_3$), so as to obtain Example Compound 2 (240 mg, 0.435 mmol, 47% yield), as a yellow powder.

$^1$H-NMR (CDCl$_3$ 400 MHz) δ: 8.37 (s, 2H), 4.14 (t, J=7.6 Hz, 4H), 1.70 (m, 4H), 1.44-1.20 (m, 28H), 0.87 (t, J=6.8 Hz, 6H); $^{13}$H-NMR (DMSO-d$_6$, 400 MHz) δ: 162.7, 159.3, 136.0, 131.0, 130.9, 124.1, 41.3, 32.0, 29.6(9), 29.6(6), 29.5, 29.4, 28.4, 27.2, 22.8, 14.3.

Example Compound 3: Synthesis of 2,6-dihexylthieno[2,3,4,5-lmn][3,8]phenanthroline-1,3,5,7(2H,6H)-tetraone

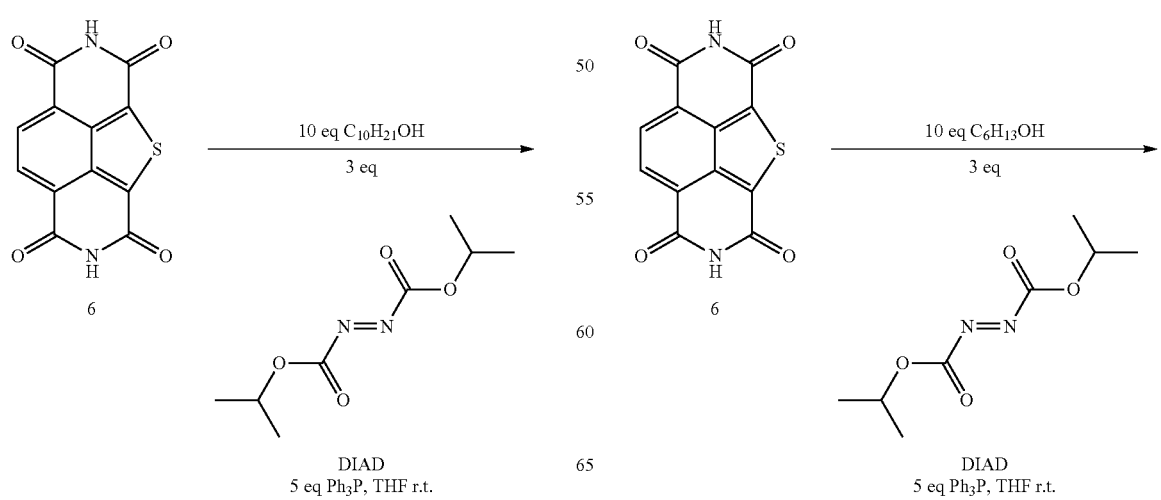

-continued

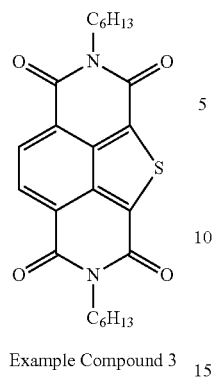

Example Compound 3

Compound "6" (250 mg, 0.918 mmol), normal hexanol (1.14 mL, 9.18 mmol), triphenylphosphine (1.20 g, 4.59 mmol), and 25 mL of THF were added to the reaction vessel, the temperature was cooled to 0° C. under an argon atmosphere, and diisopropyl azodicarboxylate (0.533 mL, 2.75 mmol) was added dropwise. The temperature of the reaction solution was returned to room temperature, and stirring was performed for one hour. Thereafter, 10 mL of diluted hydrochloric acid was added to the reaction solution to stop the reaction. The organic layer was extracted and washed with ethyl acetate and saline, and concentration was performed under reduced pressure. A concentrated residue was purified by silica gel column chromatography (toluene), gel permeation chromatography (GPC), and recrystallization (methanol/CHCl$_3$), so as to obtain Example Compound 3 (230 mg, 0.522 mmol, 52% yield), as a yellow powder.

$^1$H-NMR (CDCl$_3$ 400 MHz) δ: 8.37 (s, 2H), 4.15 (t, J=7.6 Hz, 4H), 1.70 (m, 4H), 1.49-1.28 (m, 12H), 0.90 (t, J=6.8 Hz, 6H); $^{13}$H-NMR (DMSO-d6, 400 MHz) δ: 162.7, 159.3, 136.0, 131.0, 130.9, 124.1, 41.3, 31.6, 28.4, 26.8, 22.7, 14.2.

Example Compound 4

Example Compound 4 was synthesized in the following method.

Compound 7: Synthesis of bis(2,4,6-trichlorophenyl)-1,3-bis(dimethylcarbamoyl) benzo[c]thiophene-4,7-dicarboxylate

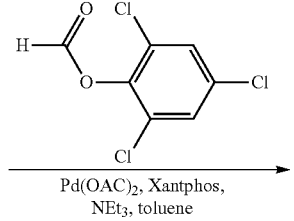

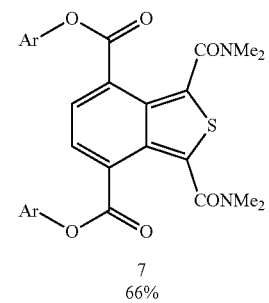

7
66%

Compound "5" (2.50 g, 5.76 mmol), 2,4,6-trichlorophenyl formate (10.4 g, 4.61 mmol), palladium (II) acetate (64.7 mg, 0.288 mmol), 4,5-bis(diphenylphosphino)-9,9-dimethylxanthene (333 mg, 0.576 mmol), and 30 mL of toluene were introduced into a Schlenk tube, and degassing and argon gas substitution were performed. Triethylamine (6.39 mL, 4.61 mmol) was added to the reaction solution under an argon atmosphere, heating was performed to 100° C., and stirring was performed for 12 hours. The temperature was cooled to the room temperature, and the reaction solution was added to water. The organic layer was extracted and washed with ethyl acetate and saline, and concentration was performed under reduced pressure. The concentrated residue was purified by silica gel column chromatography (ethylacetate:CHCl$_3$=1:1), so as to obtain Compound "7" (2.73 g, 3.77 mmol, 66% yield) as a pale yellow solid.

$^1$H-NMR (CDCl$_3$, 400 MHz) δ: 8.39 (s, 2H), 7.45 (s, 4H), 3.07 (s, 6H), 2.98 (s, 6H);

Compound 8: Synthesis of N3,7-bis(2,2,3,3,4,4,4-heptafluorobutyl)-N2,N2-dimethyl-6,8-dioxo-7,8-dihydro-6H-thieno [2,3,4-de]isoquinoline-2,3-dicarboxamide

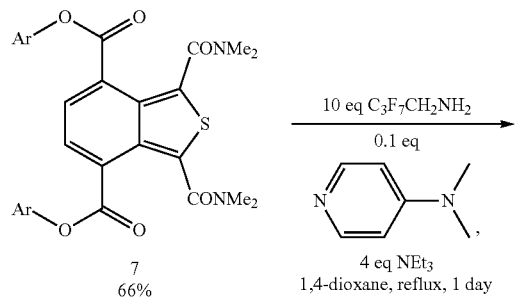

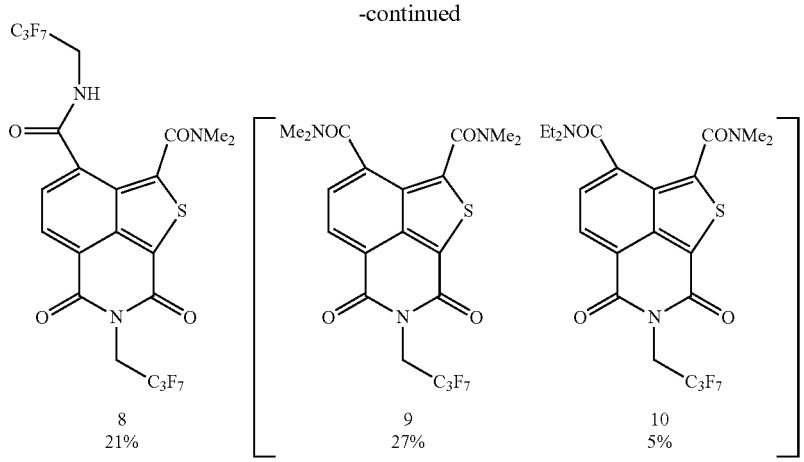

8
21%

9
27%

10
5%

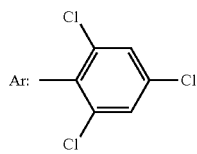

1H,1H-heptafluorobutylamine (0.923 mL, 6.91 mmol), N,N-dimethyl-4-aminopyridine (8.4 mg, 0.0691 mmol), and triethylamine were added to a suspension of Compound "7" (500 mg, 0.691 mmol) in 1,4-dioxane (8.25 mL) at room temperature. The reaction solution was heated to 100° C., and stirring was performed for 24 hours. The temperature was cooled to the room temperature, and the reaction solution was added to 10 mL of diluted hydrochloric acid. The organic layer was extracted and washed with ethyl acetate and saline, and concentration was performed under reduced pressure. The concentrated residue was purified by silica gel column chromatography (hexane:ethylacetate=1: 1), so as to obtain Compound "8" (100 mg, 0.147 mmol, 21% yield) as a yellow powder. Compound "9" (100 mg, 0.190 mmol, 27% yield) and Compound "10" (20 mg, 0.036 mmol, 5% yield) were obtained as byproducts.

8: $^1$H-NMR (CDCl$_3$, 400 MHz) δ: 8.09 (d, J=7.2 Hz, 1H), 7.49 (d, J=7.2 Hz, 1H), 6.97 (brs, 1H), 4.94 (t, J=15.6 Hz, 2H), 4.16 (td, J=14.6, 6.4 Hz, 2H), 3.16 (s, 3H), 3.10 (s, 3H); $^{19}$F-NMR (CDCl$_3$, 400 MHz) δ: −80.37, −80.41, −80.48, −80.51;

Byproduct 9: $^1$H-NMR (CDCl$_3$, 400 MHz) δ: 8.64 (d, J=7.2 Hz, 1H), 8.40 (d, J=7.2 Hz, 1H), 4.96 (t, J=15.6 Hz, 2H), 3.16 (brs, 3H), 3.12 (s, 3H), 3.01 (brs, 3H), 2.93 (s, 3H);

Byproduct 10: $^1$H-NMR (CDCl$_3$, 400 MHz) δ: 8.31 (d, J=7.2 Hz, 1H), 8.28 (d, J=7.2 Hz, 1H), 4.96 (t, J=15.6 Hz, 2H), 3.56 (q, J=7.2 Hz, 2H), 3.29 (q, J=7.2 Hz, 2H), 3.16 (s, 3H), 3.04 (s, 3H), 1.32 (t, J=7.2 Hz, 3H), 1.16 (t, J=7.2 Hz, 3H); $^{19}$F-NMR (CDCl$_3$, 400 MHz) δ: −80.34, −80.37;

Example Compound 4: Synthesis of 2,6-bis(2,2,3,3,4,4,4-heptafluorobutyl)thieno[2,3,4,5-lmn][3,8]phenanthroline-1,3,5,7(2H,6H)-tetraone

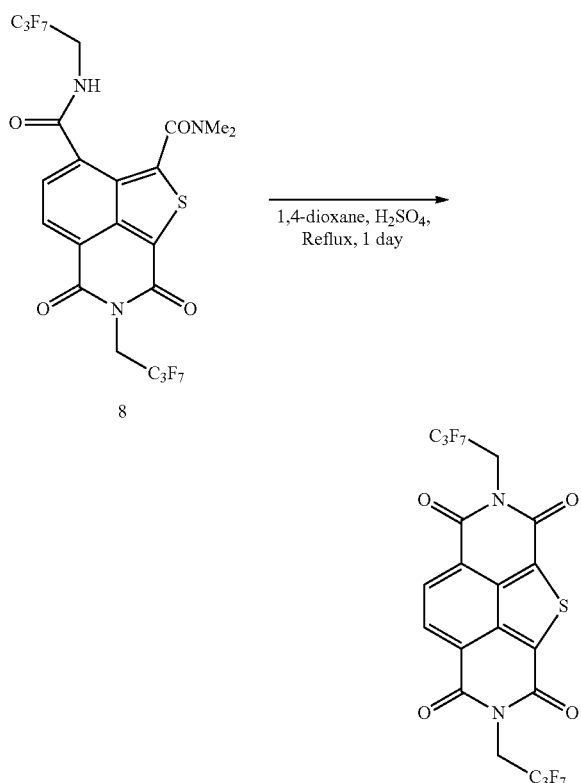

Example Compound 4

Compound "8" (100 mg, 0.147 mmol), 1,4-dioxane (2 mL), and 0.2 mL of concentrated sulfuric acid were added to a reaction vessel in an argon atmosphere, heating was performed to 100° C., and stirring was performed for 24 hours. Water was added to the reaction solution. The organic layer was extracted and washed with ethyl acetate and saline, and concentration was performed under reduced pressure. A concentrated residue was purified by gel permeation chromatography (GPC), and recrystallization (hexane/CHCl₃), so as to obtain Example Compound 4 (40 mg, 0.0629 mmol, 43% yield), as a yellow powder.

¹H-NMR (CDCl₃, 400 MHz) δ: 8.50 (s, 2H), 4.98 (t, J=15.4 Hz, 2H); ¹⁹F-NMR (CDCl₃, 400 MHz) δ: −80.33, −80.36;

Example Compound 5

Example Compound 5 was synthesized in the following method.

Compound 12: Synthesis of 4,7-dibromo-5-chloro-N¹,N¹,N³,N³-tetramethylbenzo[c]thiophene-1,3-dicarboxamide

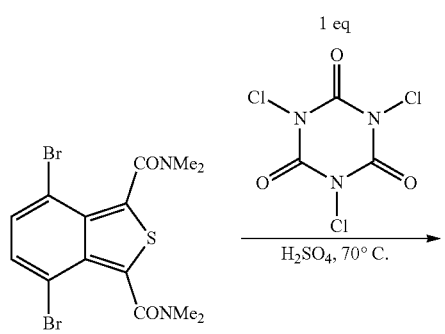

Trichloroisocyanuric acid (428 mg, 1.84 mmol) was added to 48 mL of a concentrated sulfuric acid solution of Compound "5" (800 mg, 1.84 mmol), and the mixture was heated to 70° C. and stirred for two hours. The reaction solution was poured into 300 mL of ice water to stop the reaction. The organic layer was extracted and washed with ethyl acetate and saline, and concentration was performed under reduced pressure. The residue of isocyanuric acid was removed by purifying the concentrated residue by silica gel column chromatography (hexane:acetone=1:1). A mixture including the obtained compound "12" and a byproduct was used in the subsequent reaction.

Compound 13: Synthesis of 5-chloro-4,7-dicyano-N¹,N¹,N³,N³-tetramethylbenzo[c]thiophene-1,3-dicarboxamide

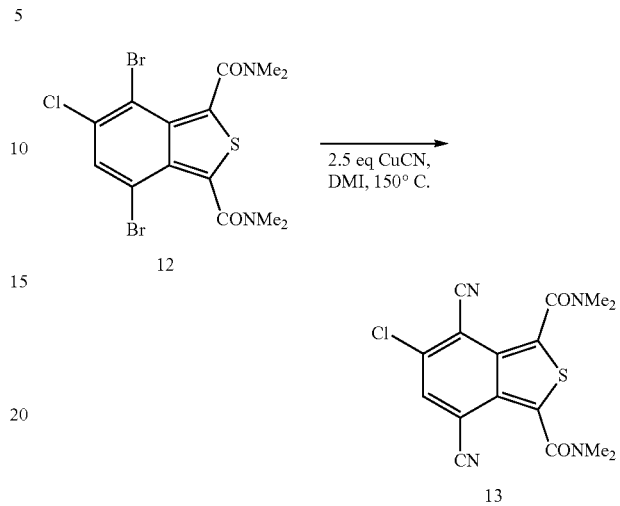

A reaction mixture containing Compound "12" (780 mg), copper cyanide (I) (372 mg, 4.15 mmol), and 5.7 mL of 1,3-dimethyl-2-imidazolidinone were introduced to a Schlenk tube, and degassing and argon gas replacement were performed. The Schlenk tube was heated to 150° C., and stirring was performed for 3 hours. The temperature was cooled to the room temperature, and the reaction solution was added to water. The organic layer was extracted and washed with ethyl acetate and saline, and concentration was performed under reduced pressure. The concentrated residue was purified by silica gel column chromatography (hexane:acetone=1:1), so as to obtain Compound "13" (330 mg, 0.915 mmol, 50% yield in 2 steps) as a yellow solid.

¹H-NMR (CDCl₃, 400 MHz) δ: 7.68 (s, 2H), 3.24 (s, 6H), 3.00 (s, 6H);

Compound 14: Synthesis of 8-chlorothieno[2,3,4,5-lmn][3,8]phenanthroline-1,3,5,7(2H,6H)-tetraone

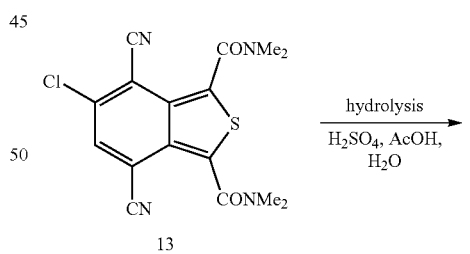

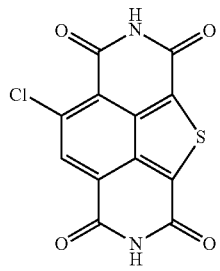

At room temperature, Compound "13" (330 mg, 0.915 mmol) was added to a mixed solvent of acetic acid (2.4 mL) and water (1.0 mL), and 0.6 mL of concentrated sulfuric acid was further added dropwise. The reaction solution was heated to 100° C., and stirring was performed for 3 hours. After the temperature was cooled to room temperature, the precipitate was filtered and washed with water and ethyl acetate, to obtain Compound "14" (153 mg, 0.50 mmol, 55% yield) as a yellow powder.

$^1$H-NMR (CDCl$_3$, 400 MHz) δ: 12.1 (s, 1H), 12.0 (s, 1H), 8.21 (s, 1H);

Example Compound 5: Synthesis of 8-chloro-2,6-dicyclohexylthieno[2,3,4,5-lmn][3,8]phenanthroline-1,3,5,7(2H,6H)-tetraone

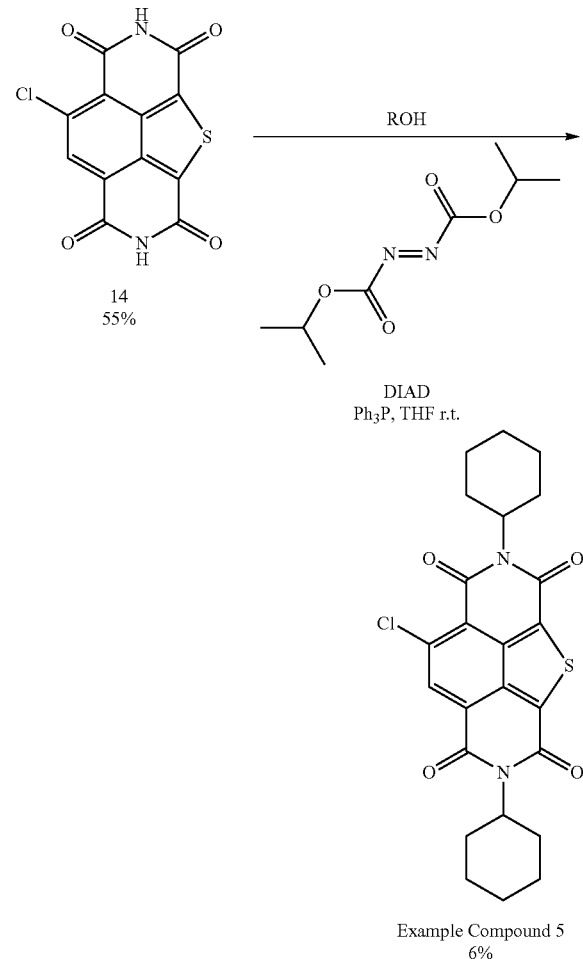

Example Compound 5
6%

Compound "14" (150 mg, 0.489 mmol), cyclohexanol (0.523 mL, 4.90 mmol), triphenylphosphine (1.29 g, 4.90 mmol), 15 mL of THF were added to the reaction vessel, the temperature was cooled to 0° C. under an argon atmosphere, and diisopropyl azodicarboxylate (0.573 mL, 2.95 mmol) was added dropwise. The reaction solution was returned to room temperature, and stirring was performed for three hours. Thereafter, 10 mL of diluted hydrochloric acid was added to the reaction solution to stop the reaction. The organic layer was extracted and washed with ethyl acetate and saline, and concentration was performed under reduced pressure. A concentrated residue was purified by silica gel column chromatography (hexane:CHCl$_3$=1:1), gel permeation chromatography (GPC), and recrystallization (methanol/CHCl$_3$), so as to obtain Example Compound 5 (2.97× 10$^{-5}$ mol, 6% yield), as a yellow powder.

$^1$H-NMR (CDCl$_3$ 400 MHz) δ: 8.30 (s, 1H), 4.97 (m, 2H), 2.49 (m, 4H), 1.90 (br d, J=13.6 HZ, 4H), 1.72 (br d, J=11.2 HZ, 6H), 1.51-1.22 (m, 6H);

Compound 15: Synthesis of 4,5,7-tribromo-N$^1$,N$^1$,N$^3$,N$^3$-tetramethylbenzo[c]thiophene-1,3-dicarboxamide

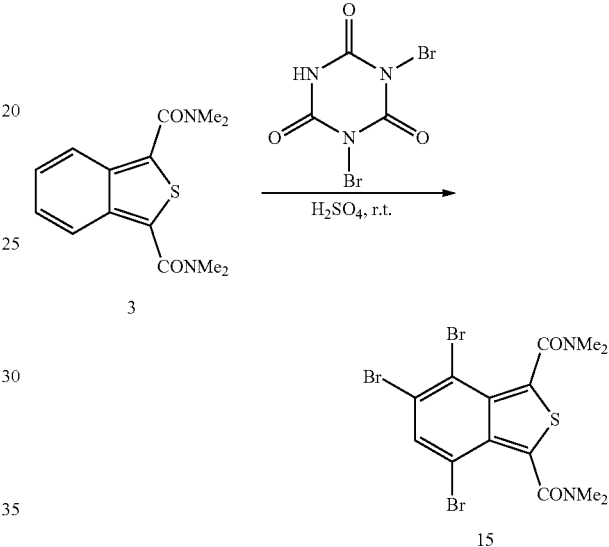

Dibromoisocyanuric acid (12.1 g, 42.3 mmol) was added to a 288 mL of concentrated sulfuric acid solution of Compound "3" (7.30 g, 26.4 mmol) at room temperature, and the mixture was stirred for 30 minutes. Thereafter, the reaction solution was poured into 500 mL of ice water to stop the reaction. The organic layer was extracted and washed with ethyl acetate and saline, and concentration was performed under reduced pressure. The concentrated residue was purified by silica gel column chromatography (ethyl acetate), so as to obtain a reaction mixture including Compound "15" as a pale yellow solid. This reaction mixture was used in the subsequent reaction without change.

Compound 16: Synthesis of 5-bromo-4,7-dicyano-N$^1$,N$^1$,N$^3$,N$^3$-tetramethylbenzo[c]thiophene-1,3-dicarboxamide

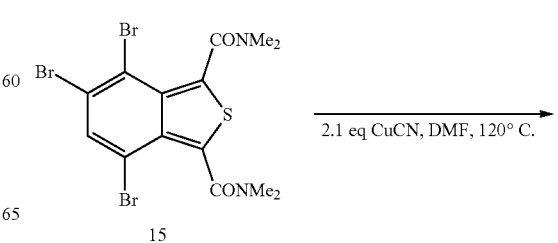

-continued

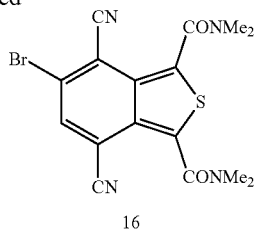

16

A reaction mixture containing Compound "15" (11.3 g), copper cyanide (I) (4.28 g, 47.8 mmol), and 45 mL of dimethylformamide were introduced to a Schlenk tube, and degassing and argon gas replacement were performed. The reaction solution was heated to 120° C., and stirring was performed for 3 hours. The temperature was cooled to the room temperature, and water was added to the reaction solution. The organic layer was extracted and washed with ethyl acetate and saline, and concentration was performed under reduced pressure. The concentrated residue was purified by silica gel column chromatography (ethyl acetate), so as to obtain Compound "16" (2.60 g, 6.42 mmol, 24% yield in 2 steps) as a pale yellow solid.

$^1$H-NMR (CDCl$_3$, 400 MHz) δ: 7.78 (s, 2H), 3.22 (s, 6H), 2.98 (s, 6H);

Compound 17: Synthesis of 8-bromothieno[2,3,4,5-lmn][3,8]phenanthroline-1,3,5,7(2H,6H)-tetraone

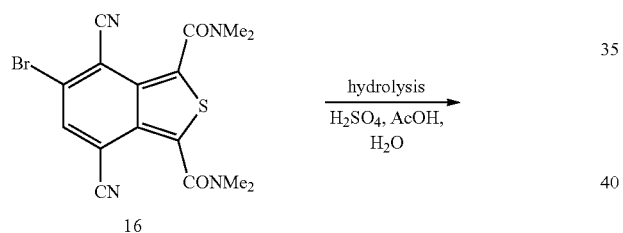

16

At room temperature, Compound "16" (1.6 g, 3.95 mmol) was added to a mixed solvent of acetic acid (10.3 mL) and water (4.38 mL), and 2.6 ml of concentrated sulfuric acid was further added dropwise. The reaction solution was heated to 100° C., and stirring was performed for four hours. After the temperature was cooled to room temperature, the precipitate was filtered and washed with water and ethyl acetate, to obtain Compound "17" (1.25 g, 3.56 mmol, 90% yield) as a yellow powder.

$^1$H-NMR (CDCl$_3$, 400 MHz) δ: 12.0 (1) (s, 1H), 11.9 (5) (s, 1H), 8.24 (s, 1H);

Example Compound 6: Synthesis of 8-bromo-2,6-dicyclohexylthieno[2,3,4,5-lmn][3,8]phenanthroline-1,3,5,7(2H,6H)-tetraone

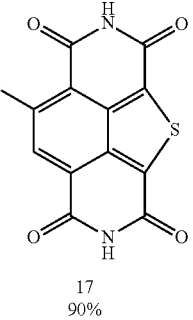

17
90%

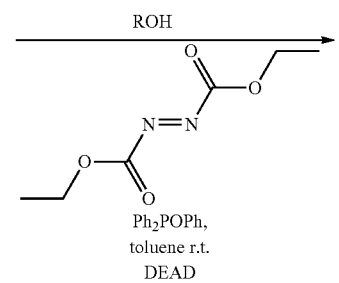

Ph$_2$POPh,
toluene r.t.
DEAD

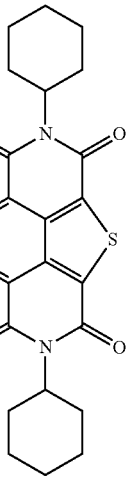

Example Compound 6
62%

Compound "17" (350 mg, 0.997 mmol), cyclohexanol (2.12 mL, 19.9 mmol), phenoxy diphenylphosphine (2.15 ml, 9.97 mmol), and 270 mL of toluene were added to the reaction vessel, the temperature was cooled to 0° C. under an argon atmosphere, and diethyl azodicarboxylate (1.57 mL, 9.97 mmol) was added dropwise. The reaction solution was returned to room temperature, and stirring was performed for three hours. Thereafter, 10 mL of diluted hydrochloric acid was added to the reaction solution to stop the reaction. The organic layer was extracted and washed with ethyl acetate and saline, and concentration was performed under reduced pressure. A concentrated residue was purified by silica gel column chromatography (toluene), gel permeation chromatography (GPC), and recrystallization (methanol/CHCl$_3$), so as to obtain Example Compound 6 (270 mg, 0.619 mmol, 62% yield), as a yellow powder.

$^1$H-NMR (CDCl$_3$ 400 MHz) δ: 8.37 (s, 1H), 4.96 (m, 2H), 2.48 (m, 4H), 1.89 (br d, J=13.6 HZ, 4H), 1.71 (br d, J=11.2 HZ, 6H), 1.52-1.19 (m, 6H);

Example Compound 7: Synthesis of 2,6-dicyclohexyl-1,3,5,7-tetraoxo-1,2,3,5,6,7-hexahydrothieno[2,3,4,5-lmn][3,8]phenanthroline-8-carbonitrile

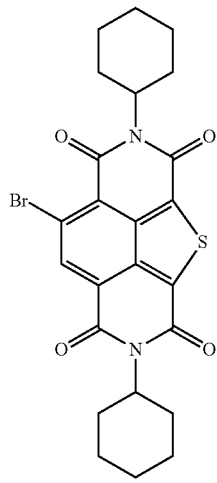

Example Compound 6

CuCN, DMF, 100° C. →

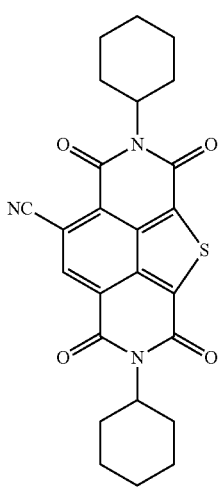

Example Compound 7
19%

Example Compound 6 (175 mg, 0.340 mmol), copper cyanide (I) (43.1 mg, 0.481 mmol), and 3.5 mL of dimethylformamide were introduced to a Schlenk tube, and degassing and argon gas replacement were performed. The reaction solution was heated to 100° C., and stirring was performed for three hours. The temperature was cooled to the room temperature, and water was added to the reaction solution. The organic layer was extracted and washed with ethyl acetate and saline, and concentration was performed under reduced pressure. A concentrated residue was purified by silica gel column chromatography (chloroform), gel permeation chromatography (GPC), and recrystallization (methanol/CHCl$_3$), so as to obtain Example Compound 7 (30 mg, 0.065 mmol, 19% yield), as a yellow powder.

$^1$H-NMR (CDCl$_3$ 400 MHz) δ: 8.04 (s, 1H), 4.93 (m, 2H), 2.49 (m, 4H), 1.85 (br d, J=13.6 HZ, 4H), 1.69 (br d, J=11.2 HZ, 6H), 1.52-1.20 (m, 6H);

Compound 18: Synthesis of benzo[c]thiophene-1,3,4,7-tetracarboxylic acid

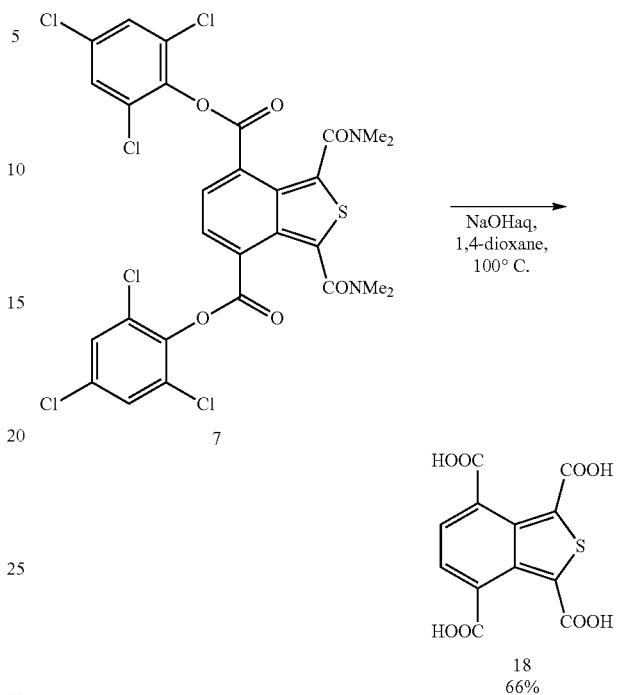

At room temperature, a 25 w/v % sodium hydroxide aqueous solution (49 ml) was added dropwise to a 1,4-dioxane solution (49 ml) of Compound "7" (3.52 g, 4.87 mmol). The reaction solution was heated to 100° C., and stirring was performed for two days. After the temperature was cooled to room temperature, the reaction solution was neutralized with concentrated hydrochloric acid, the precipitate was filtered and washed with water and acetone, to obtain Compound "18" (1.00 g, 3.22 mmol, 66% yield) as a white solid.

$^1$H-NMR (DMSO-d$_6$, 400 MHz) δ: 7.81 (s, 2H);

Compound 19: Synthesis of 2,6-dioxa-4-thiacyclopenta[def]phenanthrene-1,3,5,7-tetraone

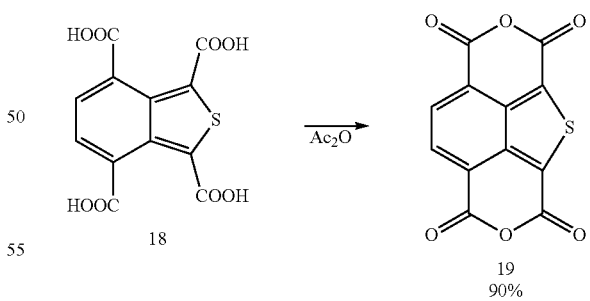

At room temperature, Compound "18" (1.00 g, 3.22 mmol) was added to acetic anhydride (100 ml), was heated to 120° C., and was stirred for one hour. After the temperature was cooled to room temperature, the solvent was removed by concentration under reduced pressure. The concentrated residue was dispersed in ethyl acetate, and the dispersed solid was filtered and washed with ethyl acetate to obtain Compound "19" (800 mg, 2.92 mmol, 90% yield) as yellowish green solid.

$^1$H-NMR (DMSO-d$_6$, 400 MHz) δ: 7.81 (s, 2H);

Example Compound 8: Synthesis of 2,6-diphenylth-ieno[2,3,4,5-lmn][3,8]phenanthroline-1,3,5,7(2H,6H)-tetraone

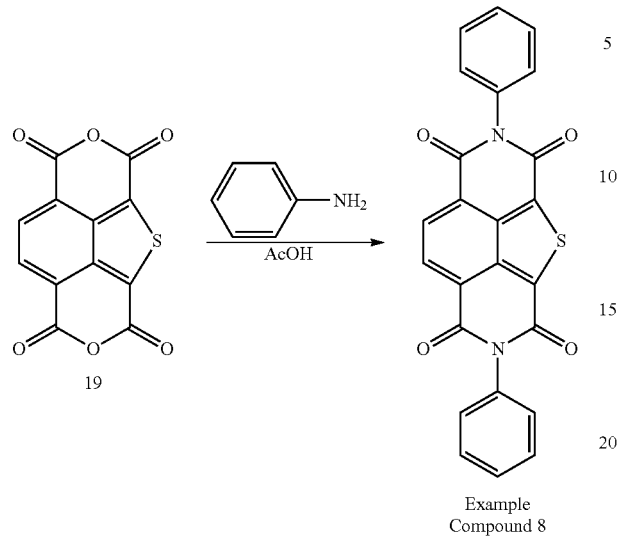

Example Compound 8

Compound 19 (100 mg, 0.365 mmol), aniline (74.7 mg, 0.802 mmol), and 3 mL of acetic acid were introduced into a reaction vessel, and argon gas replacement was performed. The reaction solution was heated to 110° C., and stirring was performed for six hours. The temperature was cooled to the room temperature, and the reaction solution was added to water. The organic layer was extracted and washed with ethyl acetate and saline, and concentration was performed under reduced pressure. A concentrated residue was purified by silica gel column chromatography (toluene), gel permeation chromatography (GPC), and recrystallization (methanol/CHCl$_3$), so as to obtain Example Compound 8 (39 mg, 0.092 mmol, 25% yield), as a yellow powder.

$^1$H-NMR (CDCl$_3$ 400 MHz) δ: 8.28 (s, 2H), 7.45-7.18 (m, 10H)

Example Compound 9: Synthesis of 2,6-dicyclohexyl-3,7-dithiooxo-2,3,6,7tetrahydrothieno[2,3,4,5-lmn][3,8]phenanthroline-1,5-dione and Example Compound 10: 2,6-dicyclohexyl-1,7-dithiooxo-1,2,6,7tetrahydrothieno[2,3,4,5-lmn][3,8]phenanthroline-3,5-dione

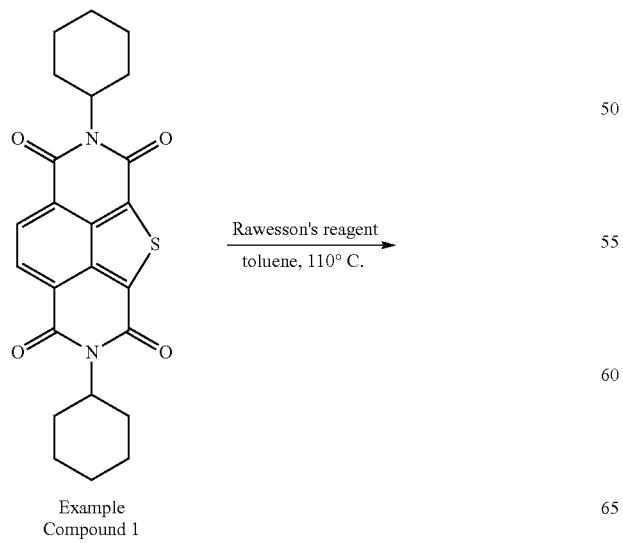

Example Compound 1

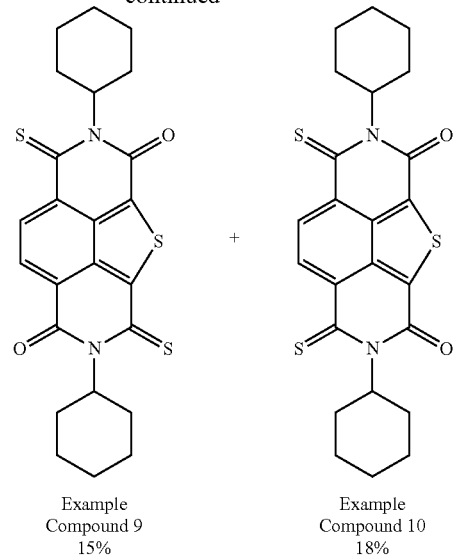

Example Compound 9
15%

Example Compound 10
18%

Example Compound 1 (200 mg, 0.458 mmol), a Rawesson's reagent (741 mg, 1.83 mmol), and 40 mL of toluene were introduced to a Schlenk tube, and degassing and argon gas replacement were performed. The reaction solution was heated to 110° C., and stirring was performed for six hours. The temperature was cooled to the room temperature, and water was added to the reaction solution. The organic layer was extracted and washed with chloroform and saline, and concentration was performed under reduced pressure. A concentrated residue was purified by silica gel column chromatography (chloroform), gel permeation chromatography (GPC), and recrystallization (methanol/CHCl$_3$), so as to obtain Example Compound 9 (33 mg, 0.070 mmol, 15% yield) and Example Compound 10 (38 mg, 0.081 mmol, 18% yield) as red powders.

Example Compound 9 $^1$H-NMR (CDCl$_3$ 400 MHz) δ: 8.13 (d, J=7.5 Hz, 1H), 7.62 (d, J=7.5 Hz, 1H), 4.87 (tt, J=12.5 and 3.5 Hz, 2H), 2.52 (qd, J=12.5 and 3.5 Hz, 4H), 1.91 (br d, J=13.5 HZ, 4H), 1.72 (br d, J=12.5 HZ, 6H), 1.52-1.21 (m, 6H);

Example Compound 10 δ: 7.58 (s, 2H), 4.96 (tt, J=12.4 and 3.5 Hz, 2H), 2.49 (qd, J=12.4 and 3.5 Hz, 4H), 1.90 (br d, J=13.2 HZ, 4H), 1.725 (br d, J=12.4 HZ, 6H), 1.54-1.23 (m, 6H);

Compound 21: Synthesis of benzo[c]selenophene-1,3-dicarbonitrile

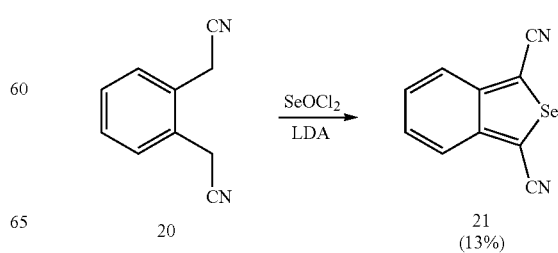

21
(13%)

A n-butyllithium 1.6 mol/L heptane solution (87.3 mL, 227 mmol) was added dropwise to diisopropylamine (22.97 g, 227 mmol) of a 250 mL THF solution under an argon atmosphere at −78° C. and was stirred for 15 minutes, so as to prepare a lithium diisopropylamide solution. THF (250 ml) of 2,2'-(1,2-phenylene) diacetonitrile ("Compound 20") (11.8 g, 75.5 mmol) was added dropwise to this solution and was stirred for 15 minutes, seleninyl dichloride (25 g, 151 mmol) was further added dropwise, a portion of the solution was quenched with water, the organic layer was extracted and washed with ethyl acetate and saline, concentration was performed under reduced pressure, and the generation of benzo[c]thiophene (Compound "2") was checked by Nuclear Magnetic Resonance (NMR). This reaction solution was used for the subsequent reaction without change.

The reaction solution was cooled to −78° C. under an argon atmosphere, N,N,N',N'-tetramethylene diamines (19.6 mL, 131 mmol) was added, a 1.6 mol/L THF solution of n-butyllithium (71.8 mL, 115 mmol) was added dropwise, and the solution was stirred for 30 minutes. After stirring, dimethylcarbamoyl chloride (15.0 mL, 164 mmol) was added dropwise, and the reaction solution was returned to room temperature and was stirred for 10 hours. The reaction was stopped by adding water to the reaction solution, the organic layer was extracted and washed with ethyl acetate and saline, and concentration was performed under reduced pressure. The concentrated residue was purified by silica gel column chromatography (CHCl$_3$:acetone=4:1), so as to obtain Compound "21" (2.28 g, 9.87 mmol, 13% yield) as a pale yellow solid.

$^1$H-NMR (CDCl$_3$, 400 MHz) δ: 7.78 (m, 2H), 7.53 (m, 2H)

Compound 22: Synthesis of benzo[c]selenophene-1,3-dicarboxamide

Compound 23: Synthesis of N$^1$,N$^1$,N$^3$,N$^3$-tetramethylbenzo[c]selenophene-1,3-dicarboxamide

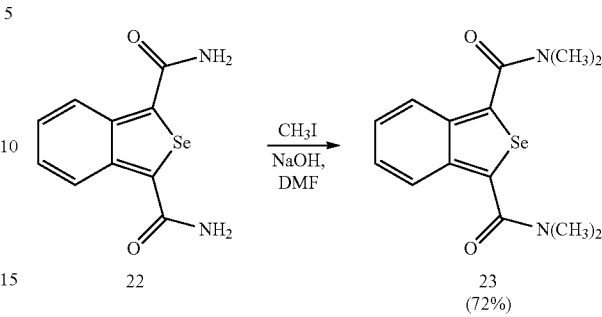

At 0° C., Compound "22" (1.25 g, 4.67 mmol), sodium hydroxide (1.13 g, 28.3 mmol), and dimethylformamide (20 ml) were added to a reaction vessel and were cooled to 0° C. Methyl iodide (1.75 ml, 54.1 mmol) was added dropwise to the reaction solution and the mixture was stirred for one hour. After reaction solution was added to water, the organic layer was extracted and washed with ethyl acetate and saline, and concentration was performed under reduced pressure, so as to obtain Compound "23" (1.1 g, 3.40 mmol, 72% yield) as a yellow solid.

$^1$H-NMR (CDCl$_3$, 400 MHz) δ: 7.38 (m, 2H), 7.05 (m, 2H), 3.13 (s, 12H)

Compound 24: Synthesis of 4,7-dibromo-N$^1$,N$^1$,N$^3$,N$^3$-tetramethylbenzo[c]selenophene-1,3-dicarboxamide

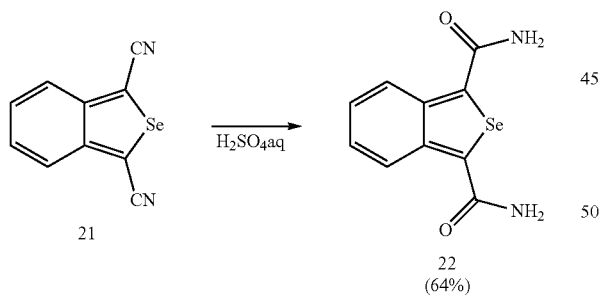

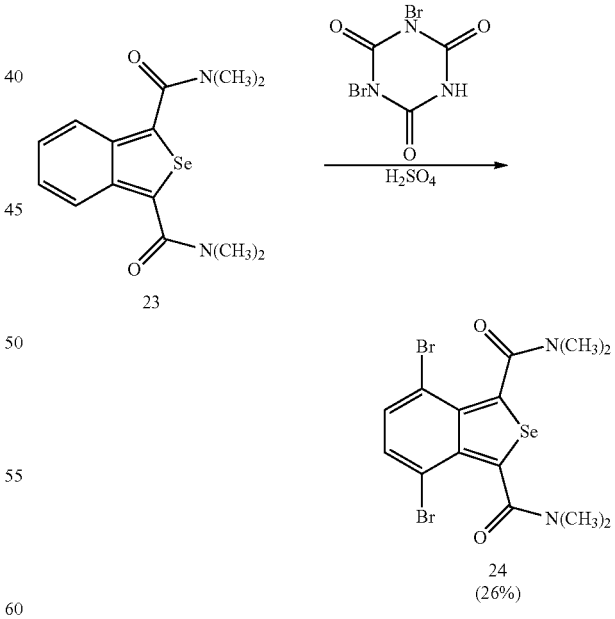

Dibromoisocyanuric acid (1.15 g, 4.00 mmol) was added to 39 mL of a concentrated sulfuric acid solution of Compound "23" (1.07 g, 3.30 mmol) at 0° C., and the mixture was stirred for 30 minutes. Thereafter, the reaction solution was poured into 300 mL of ice water to stop the reaction. The organic layer was extracted and washed with ethyl At room temperature, Compound "21" (1.9 g, 8.22 mmol) was added to acetic acid (20 mL), and 5 ml of concentrated sulfuric acid was further added dropwise. The reaction solution was heated to 90° C., and stirring was performed for one hour. After the temperature was cooled to room temperature, the reaction solution was added dropwise to 200 ml of cold water and was neutralized with 2 mol/L of an aqueous sodium hydroxide solution, and the precipitate was filtered and washed with water, so as to obtain Compound "22" (1.40 g, 5.24 mmol, 64% yield) as a yellow powder.

$^1$H-NMR (DMSO-d$_6$, 400 MHz) δ: 8.20 (m, 2H), 7.84 (brs, 4H), 7.22 (m, 2H)

acetate and saline, and concentration was performed under reduced pressure. The concentrated residue was purified by silica gel column chromatography (hexane:acetone=1:1), so as to obtain Compound "24" (433 g, 0.90 mmol, 26% yield) as a yellow solid.

$^1$H-NMR (CDCl$_3$, 400 MHz) δ: 7.12 (s, 2H), 3.16 (s, 6H), 2.86 (s, 6H)

Compound 25: Synthesis of 4,7-dicyano-N$^1$,N$^1$,N$^3$,N$^3$-tetramethylbenzo[c]selenophene-1,3-dicarboxamide

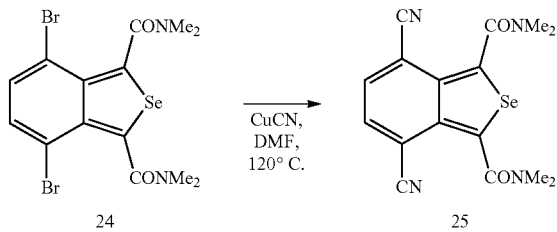

Example Compound 24 (410 mg, 0.852 mmol), copper cyanide (I) (191 mg, 2.13 mmol), and 1.68 mL of dimethylformamide were introduced to a Schlenk tube, and degassing and argon gas replacement were performed. The reaction solution was heated to 120° C., and stirring was performed for 12 hours. The temperature was cooled to the room temperature, and the reaction solution was added to water. The organic layer was extracted and washed with ethyl acetate and saline, and concentration was performed under reduced pressure. The concentrated residue was purified by silica gel column chromatography (hexane:ethyl acetate=1:1), so as to obtain Compound "25" (123 mg, 0.329 mmol, 39% yield) as a yellow solid.

$^1$H-NMR (CDCl$_3$, 400 MHz) δ: 7.53 (s, 2H), 3.23 (s, 6H), 2.99 (s, 6H)

Compound 26: Synthesis of selenopheno[2,3,4,5-lmn][3,8]phenanthroline-1,3,5,7(2H,6H)-tetraone

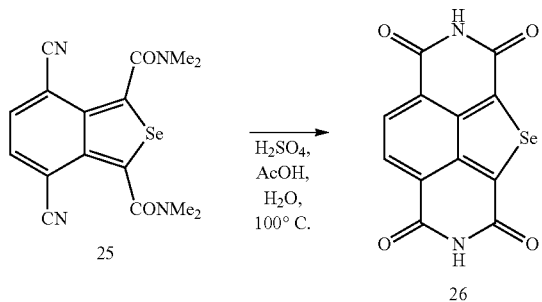

At room temperature, Compound "25" (123 mg, 0.33 mmol) was added to a mixed solvent of acetic acid (0.86 mL) and water (0.37 mL), and 0.22 ml of concentrated sulfuric acid was further added dropwise. The reaction solution was heated to 100° C., and stirring was performed for three hours. After the temperature was cooled to room temperature, the precipitate was filtered and washed with water and ethyl acetate, to obtain Compound "26" (70 mg, 0.219 mmol, 66% yield) as a yellow powder.

$^1$H-NMR (DMSO-d$_6$, 400 MHz) δ: 12.00 (s, 2H), 8.30 (s, 2H)

Example Compound 11: Synthesis of 2,6-dicyclohexylselenopheno[2,3,4,5-lmn][3,8]phenanthroline-1,3,5,7(2H,6H)-tetraone

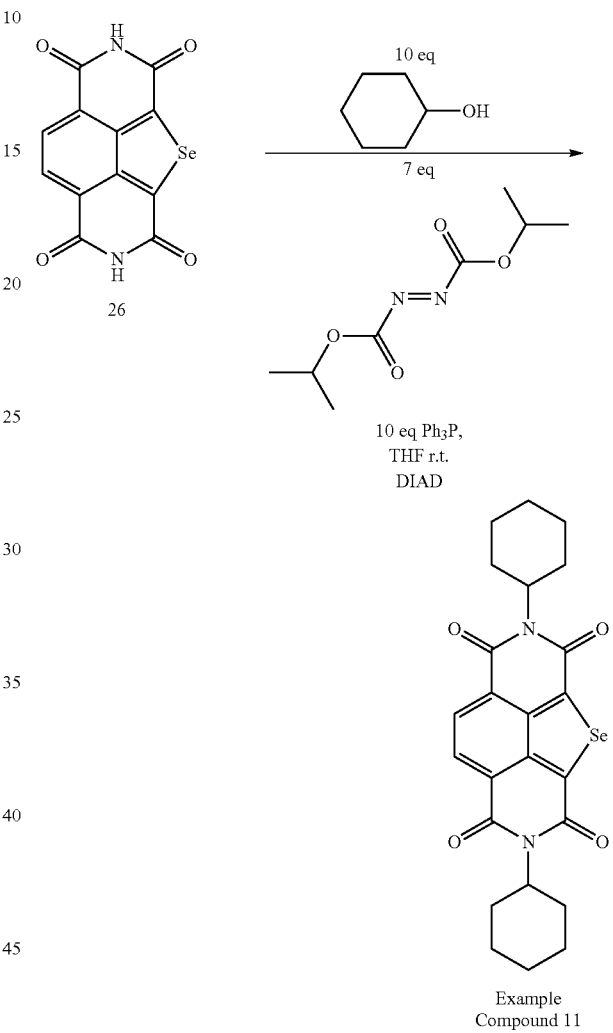

Example Compound 11

Compound "26" (50 mg, 0.157 mmol), cyclohexanol (0.167 mL, 1.57 mmol), triphenylphosphine (411 mg, 1.57 mmol), and 4.3 mL of THF were added to the reaction vessel, the temperature was cooled to 0° C. under an argon atmosphere, and diisopropyl azodicarboxylate (0.213 mL, 1.10 mmol) was added dropwise. The reaction solution was returned to room temperature, and stirring was performed for three hours. Thereafter, 10 mL of diluted hydrochloric acid was added to the reaction solution to stop the reaction. The organic layer was extracted and washed with ethyl acetate and saline, and concentration was performed under reduced pressure. The concentrated residue was dispersed in methanol, and the precipitate was filtered and washed with methanol. An obtained solid was purified by gel permeation chromatography (GPC), and recrystallization (hexane/CHCl$_3$), so as to obtain Example Compound 11 (16 mg, 0.033 mmol, 21% yield), as a yellow powder.

$^1$H-NMR (CDCl$_3$ 400 MHz) δ: 8.28 (s, 2H), 4.96 (tt, J=12.0 and 3.7 Hz, 2H), 2.49 (qd, J=12.6 and 3.3 Hz, 4H), 1.90 (br d, J=13.2 Hz, 4H), 1.72 (br d, J=12.0 HZ, 6H), 1.50-1.23 (m, 6H);

Examples 1-1 to 1-11 and Comparative Examples 1-1 to 1-3

For any one of Example Compounds 1 to 11 and Comparative Compounds 1 to 3, a 0.1 mass % solution using anisol as a solvent was prepared and heated to 50° C., so as to obtain organic thin film transistor compositions of the examples and the comparative examples.

Comparative Compounds 1 and 3 were synthesized with reference to WO2011/82234. Comparative Compound 2 was synthesized with reference to Journal of the American Chemical Society, 2013, vol. 135, #31 p. 11445 to 11448.

Example Compound 1

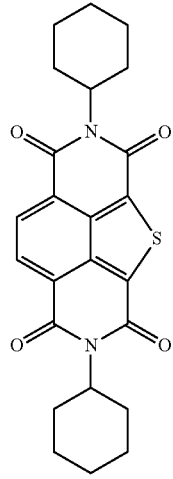

Example Compound 2

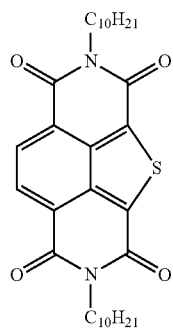

Example Compound 3

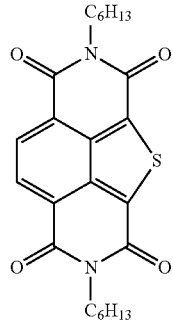

Example Compound 4

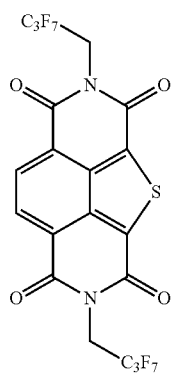

Example Compound 5

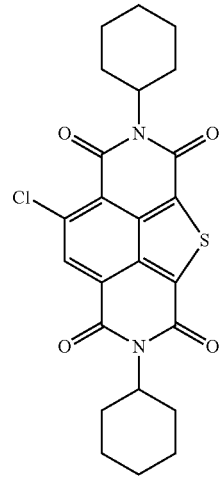

Example Compound 6

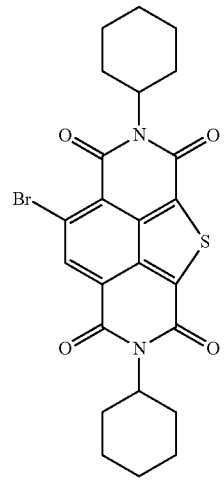

Example Compound 7
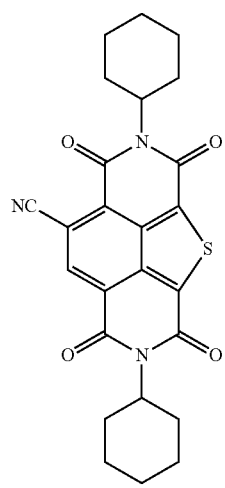
Example Compound 8
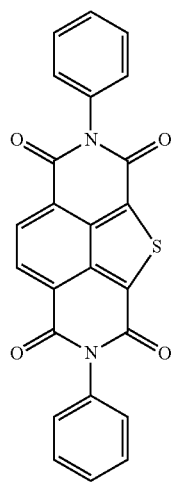
Example Compound 9
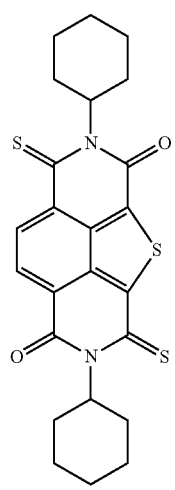
Example Compound 10
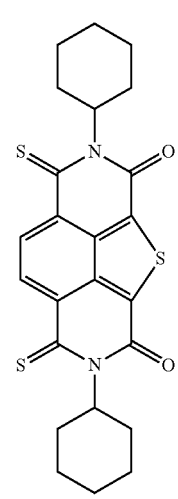
Example Compound 11
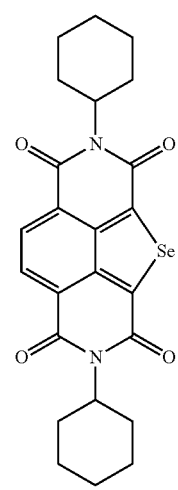
Comparative Compound 1
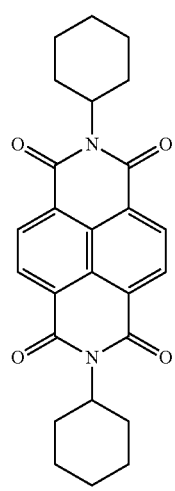

Comparative Compound 2

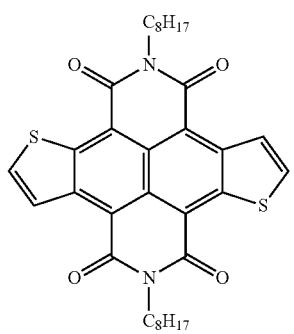

Comparative Compound 3

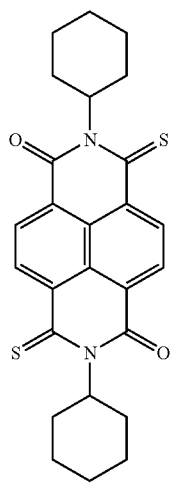

(Forming of Organic Semiconductor Film)

Figure 3:
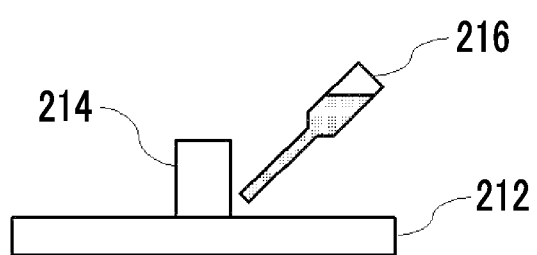
FIG. 3 is a schematic view illustrating a method of manufacturing an organic semiconductor film of examples and comparative examples.
Figure 4A:
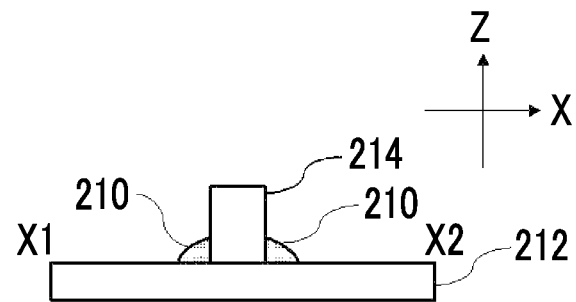
FIG. 4A is a schematic view illustrating the method of manufacturing the organic semiconductor film of examples and comparative examples.
Figure 4B:
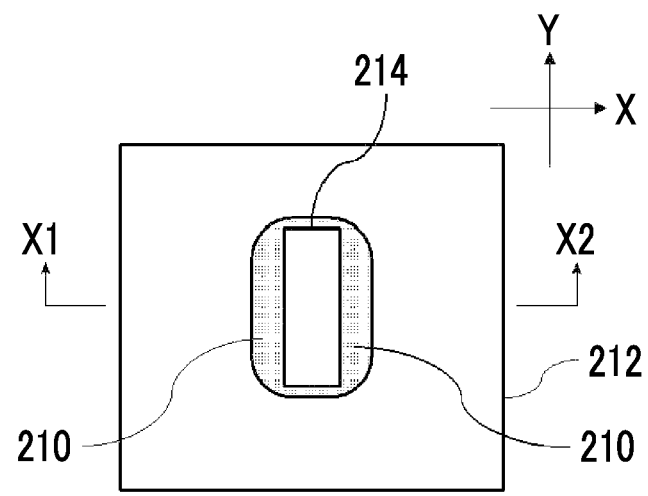
FIG. 4B is a schematic view illustrating the method of manufacturing the organic semiconductor film of examples and comparative examples.
Figure 5:
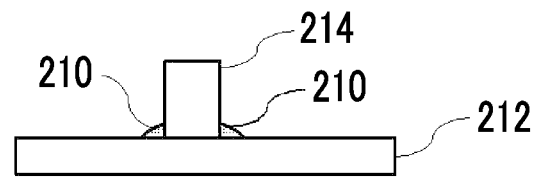
FIG. 5 is a schematic view illustrating the method of manufacturing the organic semiconductor film of examples and comparative examples.

In the examples and the comparative examples, organic semiconductor thin films were formed by the method described in FIGS. 3, 4A, 4B, and 5 (that is, FIGS. 3 to 5). FIGS. 3 to 5 are schematic views illustrating the method of manufacturing organic semiconductor films of the examples and the comparative examples. Details of the method of forming the organic semiconductor film are described below.

A 10 mm×10 mm substrate on which a 200 nm thermal oxide film of $SiO_2$ was formed on the surface of an n-type silicon substrate (0.4 mm of thickness) was used as a substrate 212. The surface of the thermal oxide film of the substrate 212 was subjected to a ultraviolet (UV)-ozone washing and a β-phenytiltrimethoxysilane treatment.

The substrate 212 and the member 214 were placed in a contact manner on the β-phenytiltrimethoxysilane treated surface of the substrate 212 in the center portion of the substrate 212 as illustrated in FIG. 3. A member 214 was made of glass and had a length of 7 mm, a width of 2 mm, and a height of 3 mm. The lateral direction (X-axis direction) in FIG. 3 was the lateral direction of the member 214, the vertical direction (Z-axis direction) in FIG. 3 was the height direction of the member 214, and the vertical direction (Y-axis direction) in FIG. 4B is a machine direction of the member 214.

The substrate 212 was heated to 95° C., and one drop (about 0.05 mL) of the organic thin film transistor composition (an organic thin film transistor composition 210 of FIGS. 3 to 5) prepared by the above method was suspended to the side portion of the member 214 by using a pippet 216 so as to come into contact with the both side of the substrate 212 and the member 214 as illustrated in FIG. 3, such that the organic thin film transistor composition 210 was added dropwise to a portion on the surface of the substrate 212 as illustrated in FIGS. 4A and 4B. A concave meniscus was formed on the interface to the member 214.

As illustrated in FIG. 5, the organic thin film transistor composition added dropwise was naturally dried in a state in which the substrate 212 and the member 214 are in contact with each other is maintained and in a state in which a positional relation between the substrate 212 and the member 214 is stopped. Thereafter, the organic thin film transistor composition was dried under reduced pressure at 90° C. for eight hours under a pressure of $10^{-3}$ MPa such that crystals of each of the above-mentioned example compounds and comparative compounds were precipitated, and thus an organic semiconductor film was formed. The precipitation of the crystals was checked by observation with a polarizing microscope. The film thickness of the obtained organic semiconductor film was 40 nm.

A mask was attached to the obtained organic semiconductor film, and a gold electrode of 40 nm was vapor-deposited, so as to obtain organic thin film transistors of examples and comparative examples for measuring carrier mobility and atmospheric stability.

(Evaluation Test)

(a) Carrier Mobility

A voltage of −80 V was applied between a source electrode and a drain electrode of each organic thin film transistor (organic TFT element), a gate voltage was changed to a range of 20 V to −100 V, an equation $I_d = (w/2L)\mu C_i(V_g - V_{th})^2$ (in the equation, L represents a gate length, w represents a gate width, $C_i$ represents a capacitance per unit area of the insulating layer, $V_g$ represents a gate voltage, and $V_{th}$ represents a threshold voltage) indicating a drain current $I_d$ was used, so as to calculate carrier mobility μ. Those having carrier mobility of $10^{-1}$ $cm^2/Vs$ or greater were evaluated as A, those having carrier mobility of $10^{-3}$ $cm^2/Vs$ or greater and less than $10^{-1}$ $cm^2/Vs$ were evaluated as B, those having carrier mobility of less than $10^{-3}$ $cm^2/Vs$ were evaluated as C, and those which were not driven as an element (no current was observed) was evaluated as D. The evaluation results of the carrier mobility are provided in a first table.

(b) Atmospheric Stability

The evaluation test of the atmospheric stability was performed as below. First, each organic thin film transistor was manufactured and was left for one week under the atmosphere and normal pressure. Carrier mobility was measured for each organic thin film transistor after being left by the same method as in "(a) Carrier mobility" described above and evaluated based on the same evaluation standard as in "(a) Carrier mobility". The evaluation results of the atmospheric stability are provided in a first table.

TABLE 7

| First table | Organic semi-conductor material | (a) Carrier mobility | (b) Atmospheric stability |
|---|---|---|---|
| Example 1-1 | Example Compound 1 | A | B |
| Example 1-2 | Example Compound 2 | B | B |
| Example 1-3 | Example Compound 3 | B | B |
| Example 1-4 | Example Compound 4 | B | B |
| Example 1-5 | Example Compound 5 | A | A |
| Example 1-6 | Example Compound 6 | A | A |
| Example 1-7 | Example Compound 7 | A | A |
| Example 1-8 | Example Compound 8 | B | B |
| Example 1-9 | Example Compound 9 | B | B |

TABLE 7-continued

| First table | Organic semi-conductor material | Evaluation result | |
|---|---|---|---|
| | | (a) Carrier mobility | (b) Atmospheric stability |
| Example 1-10 | Example Compound 10 | B | B |
| Example 1-11 | Example Compound 11 | A | A |
| Comparative Example 1-1 | Comparative Compound 1 | D | D |
| Comparative Example 1-2 | Comparative Compound 2 | B | C |
| Comparative Example 1-3 | Comparative Compound 3 | C | C |

(Evaluation Results)

From the evaluation result of the first table, it was understood that the organic thin film transistor manufactured by using the compounds (Example Compound 1 to 11) represented by Formula (1) had excellent carrier mobility and excellent atmospheric stability.

In the comparison between Example 1-1 and Example 1-2, it was found that, in a case where the substituent of at least one of "$A^{11}$" or "$A^{12}$" of Formula (1) was a cyclic alkyl group, carrier mobility of the organic thin film transistor became excellent.

In the comparison of Example 1-1 with Examples 1-5, 1-6, and 1-7, it was found that, in a case where the substituent of at least one of "$B^{11}$" or "$B^{12}$" of Formula (1) was a halogen atom or a cyano group, atmospheric stability of the organic thin film transistor became excellent.

Meanwhile, it was found that, since organic thin film transistors of Comparative Examples 1-1 and 1-3 were manufactured by using Comparative Compound 1 not having an isobenzothiophene (2-benzothiophene) structure, carrier mobility and atmospheric stability were deteriorated compared with the organic thin film transistors of the examples.

Meanwhile, it was found that, since the organic thin film transistor of Comparative Example 1-2 had a 1-benzothiophene (2-benzothiophene) structure but did not have an isobenzothiophene (2-benzothiophene) structure, atmospheric stability was deteriorated compared with the organic thin film transistors of the examples.

Examples 2-1 to 2-11 and Comparative Examples 2-1 to 2-3

In Examples 2-1 to 2-11 and Comparative Examples 2-1 to 2-3, a bottom gate/bottom contact-type organic thin film transistors were manufactured. Details thereof are described below.

A 0.1 mass % anisole solution of Example Compound 1 was heated to 100° C. and was casted on a substrate heated to 90° C. in a nitrogen atmosphere to obtain a non-light-emitting organic thin film transistor. As the substrate, a silicon substrate in a bottom gate/bottom contact structure having chrome/gold (gate width W=100 mm, gate length L=100 μm) arranged in a comb shape as source and drain electrodes and SiO2 (film thickness 200 nm) as an insulating film was used. The obtained organic thin film transistor was used as the organic thin film transistor of Example 2-1.

The organic thin film transistors of Examples 2-2 to 2-11 and Comparative Examples 2-1 to 2-3 were manufactured in the same manner as in the organic thin film transistor of Example 2-1 except for using any one of Example Compounds 2 to 11 or Comparative Compounds 1 to 3 instead of Example Compound 1.

With respect to respective organic thin film transistors of Examples 2-1 to 2-11 and Comparative Examples 2-1 to 2-3, the carrier mobility and the atmospheric stability were evaluated in the same manner as in Example 1-1. The evaluation results are provided in a second table.

TABLE 8

| Second table | Organic semi-conductor material | Evaluation result | |
|---|---|---|---|
| | | (a) Carrier mobility | (b) Atmospheric stability |
| Example 2-1 | Example Compound 1 | B | C |
| Example 2-2 | Example Compound 2 | C | C |
| Example 2-3 | Example Compound 3 | C | C |
| Example 2-4 | Example Compound 4 | B | B |
| Example 2-5 | Example Compound 5 | B | B |
| Example 2-6 | Example Compound 6 | B | B |
| Example 2-7 | Example Compound 7 | A | A |
| Example 2-8 | Example Compound 8 | C | C |
| Example 2-9 | Example Compound 9 | B | C |
| Example 2-10 | Example Compound 10 | B | C |
| Example 2-11 | Example Compound 11 | A | B |
| Comparative Example 2-1 | Comparative Compound 1 | D | D |
| Comparative Example 2-2 | Comparative Compound 2 | C | D |
| Comparative Example 2-3 | Comparative Compound 3 | C | D |

(Evaluation Results)

It was found that, even in a case where a bottom gate/bottom contact-type organic thin film transistor was manufactured, from the evaluation results of Examples 2-1 to 2-11 and Comparative Examples 2-1 to 2-3, the same tendency of Examples 1-1 to 1-11 and Comparative Examples 1-1 to 1-3 as described above were exhibited.

Examples 3-1 to 3-11 and Comparative Examples 3-1 to 3-3

A bottom gate/bottom contact type element was manufactured in the same manner as in Example 2-1, except for using a material (Material 1') containing Example Compound 1 and poly(α-methylstyrene) at a mass ratio of 1:1 instead of Example Compound 1 in the example. The obtained element was used as the organic thin film transistor of Example 3-1.

The organic thin film transistors of Example 3-2 to 3-11 and Comparative Example 3-1 to 3-3 were manufactured in the same manner as in Example 3-1 except for using any one of Example Compounds 2 to 11 or Comparative Compounds 1 to 3 instead of Example Compound 1.

With respect to respective organic thin film transistors of Examples 3-1 to 3-11 and Comparative Examples 3-1 to 3-3, the carrier mobility and the atmospheric stability were evaluated in the same manner as in Example 1-1. The evaluation results are provided in a third table.

TABLE 9

| Third table | Organic semi-conductor material | Evaluation result | |
|---|---|---|---|
| | | (a) Carrier mobility | (b) Atmospheric stability |
| Example 3-1 | Example Compound 1 | B | C |
| Example 3-2 | Example Compound 2 | C | C |
| Example 3-3 | Example Compound 3 | C | C |
| Example 3-4 | Example Compound 4 | B | C |
| Example 3-5 | Example Compound 5 | B | B |

TABLE 9-continued

| Third table | Organic semi-conductor material | Evaluation result | |
|---|---|---|---|
| | | (a) Carrier mobility | (b) Atmospheric stability |
| Example 3-6 | Example Compound 6 | B | C |
| Example 3-7 | Example Compound 7 | A | A |
| Example 3-8 | Example Compound 8 | C | C |
| Example 3-9 | Example Compound 9 | B | C |
| Example 3-10 | Example Compound 10 | B | C |
| Example 3-11 | Example Compound 11 | A | B |
| Comparative Example 3-1 | Comparative Compound 1 | D | D |
| Comparative Example 3-2 | Comparative Compound 2 | D | D |
| Comparative Example 3-3 | Comparative Compound 3 | D | D |

(Evaluation Results)

The bottom gate/bottom contact-type organic thin film transistors of Examples 3-1 to 3-11 and Comparative Examples 3-1 to 3-3 were manufactured by using each organic thin film transistor composition obtained by adding a binder polymer to each of example compounds and comparative compounds.

All of the organic thin film transistors of Examples 3-1 to 3-11 had excellent carrier mobility and excellent atmospheric stability compared with the organic thin film transistors of Comparative Examples 3-1 to 3-3.

Meanwhile, it was found that, the organic thin film transistors of Comparative Examples 3-1 and 3-3 did not have an isobenzothiophene (2-benzothiophene) structure, and thus had deteriorated carrier mobility and deteriorated atmospheric stability compared with the organic thin film transistors of Examples 3-1 to 3-11.

EXPLANATION OF REFERENCES

10: substrate
20: gate electrode
30: gate insulating film
40: source electrode
42: drain electrode
50: organic semiconductor layer (organic semiconductor film)
60: sealing layer
100,200: organic thin film transistor
210: organic thin film transistor composition
212: substrate
214: member
216: pipette

What is claimed is:

1. An organic thin film transistor comprising:
an organic semiconductor film containing a compound represented by Formula (1) or (2),

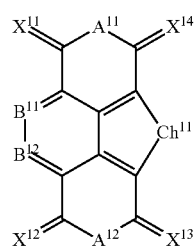

(1)

in Formula (1), $A^{11}$ and $A^{12}$ each independently represent —N($R^N$)— or —P($R^N$)—, $R^N$ represents a hydrogen atom or a substituent, and a plurality of $R^N$'s are identical to or different from each other, in Formula (1), $B^{11}$ and $B^{12}$ each independently represent —N= or —C($R^M$)=, $R^M$ represents a hydrogen atom or a substituent, and in a case where both of $B^{11}$ and $B^{12}$ are —C($R^M$)=, $R^M$ included in $B^{11}$ and $R^M$ included in $B^{12}$ may form a ring, in Formula (1), $Ch^{11}$ represents a sulfur atom, a sulfinyl group, a sulfonyl group, a selenium atom, a seleninyl group, or a selenonyl group, and in Formula (1), $X^{11}$, $X^{12}$, $X^{13}$, and $X^{14}$ each independently represent an oxygen atom or a sulfur atom,

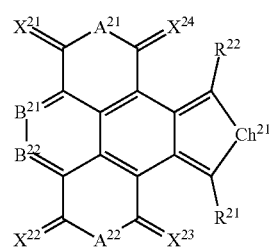

(2)

in Formula (2), $A^{21}$ and $A^{22}$ each independently represent —N($R^N$)— or —P($R^N$)—, $R^N$ represents a hydrogen atom or a substituent, and a plurality of $R^N$'s are identical to or different from each other, in Formula (2), $B^{21}$ and $B^{22}$ each independently represent —N= or —C($R^M$)=, $R^M$ represents a hydrogen atom or a substituent, and in a case where both of $B^{21}$ and $B^{22}$ are —C($R^M$)=, $R^M$ included in $B^{21}$ and $R^M$ included in $B^{22}$ may form a ring, in Formula (2), $Ch^{21}$ represents a sulfur atom, a sulfinyl group, a sulfonyl group, a selenium atom, a seleninyl group, or a selenonyl group, in Formula (2), $X^{21}$, $X^{22}$, $X^{23}$, and $X^{24}$ each independently represent an oxygen atom or a sulfur atom, and in Formula (2), $R^{21}$ and $R^{22}$ each independently represent a hydrogen atom or a substituent.

2. The organic thin film transistor according to claim 1, wherein, in Formula (1), $Ch^{11}$ is a sulfur atom or a selenium atom, and
wherein, in Formula (2), $Ch^{21}$ is a sulfur atom or a selenium atom.

3. The organic thin film transistor according to claim 1, wherein, in Formula (1), all of $X^{11}$, $X^{12}$, $X^{13}$, and $X^{14}$ are oxygen atoms, and
wherein, in Formula (2), all of $X^{21}$, $X^{22}$, $X^{23}$, and $X^{24}$ are oxygen atoms.

4. The organic thin film transistor according to claim 1, wherein, in Formula (1), $A^{11}$ and $A^{12}$ each independently represent —N($R^N$)—, and
wherein, in Formula (2), $A^{21}$ and $A^{22}$ each independently represent —N($R^N$)—.

5. The organic thin film transistor according to claim 4, wherein $R^N$ is a linear, branched, or cyclic alkyl group having 1 to 20 carbon atoms, an aryl group having 6 to 20 carbon atoms, or a heteroaryl group having 3 to 20 carbon atoms.

6. The organic thin film transistor according to claim 5, wherein $R^N$ is a cyclic alkyl group having 4 to 6 carbon atoms.

7. The organic thin film transistor according to claim 1,
wherein, in a case where at least one of $B^{11}$ or $B^{12}$ in Formula (1) is $-C(R^M)=$, at least one of $R^M$'s is a halogen atom, and
wherein, in a case where at least one of $B^{21}$ or $B^{22}$ in Formula (2) is $-C(R^M)=$, at least one of $R^M$'s is a halogen atom.

8. The organic thin film transistor according to claim 1,
wherein $R^{21}$ and $R^{22}$ in Formula (2) each independently represent a hydrogen atom, a methyl group, a halogen atom, or a cyano group.

9. A compound represented by Formula (1) or (2),

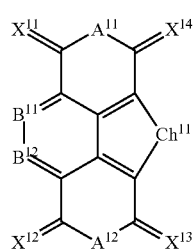
(1)

in Formula (1), $A^{11}$ and $A^{12}$ each independently represent $-N(R^N)-$, $-P(R^N)-$, or $-O-$, $R^N$ represents a hydrogen atom or a substituent, and a plurality of $R^N$'s are identical to or different from each other, in Formula (1), $B^{11}$ and $B^{12}$ each independently represent $-N=$ or $-C(R^M)=$, $R^M$ represents a hydrogen atom or a substituent, and in a case where both of $B^{11}$ and $B^{12}$ are $-C(R^M)=$, $R^M$ included in $B^{11}$ and $R^M$ included in $B^{12}$ may form a ring, in Formula (1), $X^{11}$, $X^{12}$, $X^{13}$, and $X^{14}$ each independently represent an oxygen atom or a sulfur atom, and in Formula (1), $Ch^{11}$ represents a sulfur atom, a sulfinyl group, a sulfonyl group, a selenium atom, a seleninyl group, or a selenonyl group,

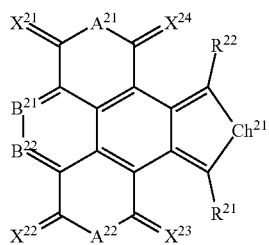
(2)

in Formula (2), $A^{21}$ and $A^{22}$ each independently represent $-N(R^N)-$, $-P(R^N)-$, or $-O-$, $R^N$ represents a hydrogen atom or a substituent, and a plurality of $R^N$'s are identical to or different from each other, in Formula (2), $B^{21}$ and $B^{22}$ each independently represent $-N=$ or $-C(R^M)=$, $R^M$ represents a hydrogen atom or a substituent, and in a case where both of $B^{21}$ and $B^{22}$ are $-C(R^M)=$, $R^M$ included in $B^{21}$ and $R^M$ included in $B^{22}$ may form a ring, in Formula (2), $Ch^{21}$ represents a sulfur atom, a sulfinyl group, a sulfonyl group, a selenium atom, a seleninyl group, or a selenonyl group, in Formula (2), $X^{21}$, $X^{22}$, $X^{23}$, and $X^{24}$ each independently represent an oxygen atom or a sulfur atom, and in Formula (2), $R^{21}$ and $R^{22}$ each independently represent a hydrogen atom or a substituent.

10. The compound according to claim 9,
wherein, in Formula (1), $Ch^{11}$ is a sulfur atom or a selenium atom, and
wherein, in Formula (2), $Ch^{21}$ is a sulfur atom or a selenium atom.

11. The compound according to claim 9,
wherein, in Formula (1), all of $X^{11}$, $X^{12}$, $X^{13}$, and $X^{14}$ are oxygen atoms, and
wherein, in Formula (2), all of $X^{21}$, $X^{22}$, $X^{23}$, and $X^{24}$ are oxygen atoms.

12. The compound according to claim 9,
wherein, in Formula (1), $A^{11}$ and $A^{12}$ each independently represent $-N(R^N)-$ or $-P(R^N)-$, and
wherein, in Formula (2), $A^{21}$ and $A^{22}$ each independently represent $-N(R^N)-$ or $-P(R^N)-$.

13. The compound according to claim 9,
wherein, in Formula (1), $A^{11}$ and $A^{12}$ each independently represent $-N(R^N)-$, and
wherein, in Formula (2), $A^{21}$ and $A^{22}$ each independently represent $-N(R^N)-$.

14. The compound according to claim 12,
wherein $R^N$ is a linear, branched, or cyclic alkyl group having 1 to 20 carbon atoms, an aryl group having 6 to 20 carbon atoms, or a heteroaryl group having 3 to 20 carbon atoms.

15. The compound according to claim 14,
wherein $R^N$ is a cyclic alkyl group having 4 to 6 carbon atoms.

16. The compound according to claim 9,
wherein, in a case where at least one of $B^{11}$ or $B^{12}$ in Formula (1) is $-C(R^M)=$, at least one of $R^M$'s is a halogen atom, and
wherein, in a case where at least one of $B^{21}$ or $B^{22}$ in Formula (2) is $-C(R^M)=$, at least one of $R^M$'s is a halogen atom.

17. The compound according to claim 9,
wherein $R^{21}$ and $R^{22}$ in Formula (2) each independently represent a hydrogen atom, a methyl group, a halogen atom, or a cyano group.

18. An organic thin film transistor material comprising:
the compound according to claim 9.

19. An organic thin film transistor composition comprising:
the compound according to claim 9.

20. The organic thin film transistor composition according to claim 19, further comprising:
a binder polymer.

21. An organic semiconductor film containing the compound according to claim 9.

22. A method of manufacturing an organic thin film transistor, comprising:
a step of coating a substrate with the organic thin film transistor composition according to claim 19 and drying the composition to form an organic semiconductor film.

* * * * *